US008623356B2

(12) United States Patent
Christopherson et al.

(10) Patent No.: US 8,623,356 B2
(45) Date of Patent: Jan. 7, 2014

(54) DEMIBODIES: DIMERIZATION-ACTIVATED THERAPEUTIC AGENTS

(75) Inventors: Richard Ian Christopherson, Paddington (AU); Jacqueline Mary Matthews, Newtown (AU); Joel Peter MacKay, Newtown (AU)

(73) Assignee: The University of Sydney, Sydney, New South Wales (AU)

( * ) Notice: Subject to any disclaimer, the term of this patent is extended or adjusted under 35 U.S.C. 154(b) by 494 days.

(21) Appl. No.: 12/095,468

(22) PCT Filed: Nov. 29, 2006

(86) PCT No.: PCT/AU2006/001810
§ 371 (c)(1),
(2), (4) Date: Oct. 16, 2008

(87) PCT Pub. No.: WO2007/062466
PCT Pub. Date: Jun. 7, 2007

(65) Prior Publication Data
US 2009/0130106 A1 May 21, 2009

Related U.S. Application Data

(60) Provisional application No. 60/741,030, filed on Nov. 29, 2005.

(30) Foreign Application Priority Data

Mar. 2, 2006 (AU) ............................... 2006901059

(51) Int. Cl.
*A61K 38/00* (2006.01)

(52) U.S. Cl.
USPC .................. 424/130.1; 424/133.1; 424/135.1; 424/138.1; 424/141.1; 530/387.1; 530/387.3

(58) Field of Classification Search
None
See application file for complete search history.

(56) References Cited

U.S. PATENT DOCUMENTS 5,837,242 A   11/1998  Holliger et al.
5,985,276 A   11/1999  Lindhofer et al.
6,129,914 A   10/2000  Weiner et al.

FOREIGN PATENT DOCUMENTS

WO   WO 95/09917        4/1995
WO   WO 2004/042404 A1  5/2004
WO   WO 2004/058821 A2  7/2004

OTHER PUBLICATIONS

Skolnick and Fetrow. From genes to protein structure and function: novel applications of computational approaches in the genomic era. Trends in Biotechnology, 2000. vol. 18, pp. 34-39.*
Burgess, Shaheen, Ravera, Jaye, Donohue, and Winkles. Possible dissociation of the heparin binding and mitogenic activities of heparin binding (acidic fibroblast) growth factor-1 from its receptor binding activities by site directed mutagenesis of a single lysine residue. Journal of Cell Biology, 1990. vol. 111, pp. 2129-2138.*
Lazar, Watanabe, Dalton and Sporn. Transforming growth factor alpha: mutation of aspartic acid 47 and leucine 48 results in different biological activities. Molecular and Cellular Biology, 1988. vol. 8, pp. 1247-1252.*
Schwartz, Burke, and Katsoyannis. A superactive insulin: [B 10-aspartic Acid] insulin (Human). Proceedings of the National Academy of Sciences, 1987. vol. 84, pp. 6408-6411.*
Lin, Wright, Hruby, and Rodbell. Structure-function relationships in glucagon: properties of highly purified Des-His1-Monoiodo-, and [Des-Asn28, Thr29] (homoserine lactone 27)-glucagon. Biochemistry, 1975. vol. 14, pp. 1559-1563.*
De Kruif and Logtenberg. Leucine zipper dimerized bivalent and bispecific scFv antibodies from a semi-synthetic antibody phage display library. Journal of Biological Chemistry, 1996. vol. 271, pp. 7630-7634.*
Kostelny, Cole, and Tso. Formation of a bispecific antibody by the use of leucine zippers. Journal of Immunology, 1992. vol. 148, pp. 1547-1553.*
Pack and Pluckthun. Miniantibodies: use of amphipathic helices to produce functional, flexibly linked dimeric Fv fragments with high avidity in *E. coli*. Biochemistry, 1992. vol. 31, pp. 1579-1584.*
Pack, Kujau, Schroeckh, Knupfer, Wenderoth, Riesenberg, and Pluckthun. Improved bivalent miniantibodies with identical avidity as whole antibodies, produced by high cell density fermentation of *E. coli*. Bio/technology, 1993. vol. 11, pp. 1271-1277.*
Alt et al (FEBS Letters, 1999, 454:90-94).*
Kruif et al (J of Biol Chem, 1996, 271:7630-7634).*
Koolwijk et al (J of Immunol, 1989, 143:1656-1662).*
Biolink Partners Ltd., Demibodies™: Dimerization-activated therapeutic antibodies (retrieved on Jan. 19, 2007). Retrieved from the Internet <URL: http://www.biolink.org.au/library/File/Demibodies.pdf>.
Coloma, M.J. and Morrison, S.L. 1997 "Design and production of novel tetravalent bispecific antibodies" *Nature Biotechnology* 15:159-163.
Heuser, C. et al. 2003 An anti-MUC1-antibody-interleukin-2 fusion protein that activates resting NK cells to lysis of MUC1-positive tumour cells *British Journal of Cancer* 89:1130-1139.
Holt, L.J. et al. 2003 "Domain antibodies: proteins for therapy" *Trends in Biotechnology* 21:484-490.

(Continued)

Primary Examiner — Sean E Aeder
Assistant Examiner — Julie Wu
(74) Attorney, Agent, or Firm — Knobbe, Martens, Olson & Bear, LLP

(57) ABSTRACT

The present invention relates generally to a set of synthetic immunointeractive molecules referred to herein as "demibodies" which are useful in targeting particular cells in a subject. More particularly, the present invention provides a set of demibodies wherein at least two molecules from within the set, each specific for a different antigen on a target cell, are required to interact together at the cell surface in order to form an active complex which directs demibody-mediated cellular or complement mediated cytotoxicity and/or reporter function and/or therapeutic activity. The demibodies of the present invention are useful in the targeting of particular cells such as cancer cells including leukemic cells, pathogens including malarial, bacterial and viral agents, and stem cells including embryonic and adult stem cells and pathogen cells. The present invention provides, therefore, methods of treatment, diagnosis and undertaking research and compositions comprising demibodies useful for same.

5 Claims, 18 Drawing Sheets

(56) References Cited

OTHER PUBLICATIONS

Zhao, Y. et al. 2005 Therapeutic applications of superantibodies, *Drug Discovery Today* 10(18):1231-1236.

Kipriyanov, S.M. et al. 2004 "Generation and production of engineered antibodies" Molecular *Biotechnology* 26:39-60.

Ohiro, Y. et al. 2002 "A homogeneous and noncompetitive immunoassay based on the enhanced fluorescence resonance energy transfer by leucine zipper interaction" *Anal Chem* 74:5786-5792.

Supplementary Partial European Search Report for European Application No. 06 81 7559, dated Oct. 20, 2010.

Xie, Z. et al. 2005 "A new format of bispecific antibody: highly efficient heterodimerization, expression and tumor cell lysis" *J Immunol Methods* 296:95-101.

Batard, P. et al. 2002 "Use of Phycoerythrin and Allophycocyanin for Fluorescence Resonance Energy Transfer Analyzed by Flow Cytometry: Advantages and Limitations" *Cytometry* 48: 97-105.

Japanese Patent Office Action in corresponding Japanese Application No. 2008-542559, dated Feb. 9, 2012.

Sondermann, P. et al. 2000 "The 3.2-Å crystal structure of the human IgG1 Fc fragment-FcγRIII complex" *Nature* 406: 267-273.

\* cited by examiner

Trx-CD45-mOrange-e3
MSDKIIHLTDDSFDTDVLKADGAILVDFWAEWCGPCKMIAPILDEIADEYQGKLTVAKLN
IDQNPGTAPKYGIRGIPTLLLFKNGEVAATKVGALSKGQLKEFLDANLAGSGSGHMHHHH
HHSSGLVPRGSGMKETAAAKFERQHMDSPDLGTDDDDK<u>QVQLVESGGGLVQPGGSLKLSC
AASGFDFSRYWMSWVRQAPGKGLEWIGEINPTSSTINFTPSLKDKVFISRDNAKNTLYLQ
MSKVRSEDTALYYCARGNYYRYGDAMDYWGQGTSVTVSKISGGGGSGGGGSGGGGSGGGG
SGGGGSSDIVLTQSPASLAVSLGQRATISCRASKSVSTSGYSYLHWYQQKPGQPPKLLIY
LASNLESGVPARFSGSGSGTDFTLNIHPVEEEDAATYYCQHSRELPFTFGSGTKLEIK</u>vd
GGGGSGGGGSGGGGSGGGrsMVSKGEENNMAIIKEFMRFKVRMEGSVNGHEFEIEGEGEG
RPYEGFQTAKLKVTKGGPLPFAWDILSPQFTYGSKAYVKHPADIPDYFKLSFPEGFKWER
VMNFEDGGVVTVTQDSSLQDGEFIYKVKLRGTNFPSDGPVMQKKTMGWEASSERMYPEDG
ALKGEIKMRLKLKDGGHYTSEVKTTYKAKKPVQLPGAYIVGIKLDITSHNEDYTIVEQYE
RAEGRHSTGGMDELYKleGGGGSGGGGSGGGGSGGGTSEISALEKEISALEKEISALEKA
S

Number of amino acids: 721
Molecular weight: 76713.6
Theoretical pI: 5.86
Extinction coefficients: ($M^{-1}$ $cm^{-1}$, at 280 nm).
Ext. coefficient    97095
Abs 0.1% (=1 g/l)   1.266, assuming ALL Cys residues appear as half cystines

Figure 1A

Trx-CD20-T-Sapphire-k3
MSDKIIHLTDDSFDTDVLKADGAILVDFWAEWCGPCKMIAPILDEIADEYQGKLTVAKLN
IDQNPGTAPKYGIRGIPTLLLFKNGEVAATKVGALSKGQLKEFLDANLAGSGSGHMHHHH
HHSSGLVPRGSGMKETAAAKFERQHMDSPDLGTDDDDKMDVVMTQTPASLSASVGETVTI
TCRASGSIHNYLAWYQQKLGKSPQLLVYNAKTLADGVPSRFSGSGSGTQFSLKINSLQPE
DFGSYYCQHFWSIPWTFGGGTKLELKRGGGGGGGSGGGGSGGGGSQVQLQQSGTELVKP
VASVKMSCKASGFTFTDYNMHWVKQTPGQGLEWIGAIYPENGDTSYNQRFKGKATLTADK
SFSTAYMHLSSLTSEDTAVYFCARFYYYGSYYGALDYWGQGTSVTVSSDSGAEFEvdGGG
GSGGGGSGGGGSGGGrsMSKGEELFTGVVPILVELDGDVNGHKFSVSGEGEGDATYGKLT
LKFICTTGKLPVPWPTLVTTFSYGVMVFSRYPDHMKQHDFFKSAMPEGYVQERTIFFKDD
GNYKTRAEVKFEGDTLVNRIELKGIDFKEDGNILGHKLEYNYNSHNVYIMADKQKNGIKA
NFKIRHNIEDGGVQLADHYQQNTPIGDGPVLLPDNHYLSIQSALSKDPNEKRDHMVLLEF
VTAAGITHGMDELYKleGGGGSGGGGSGGGGSGGGtsKISALKEKISALKEKISALKEAS

Number of amino acids: 720
Molecular weight: 76888.9
Theoretical pI: 5.92
Extinction coefficients: ($M^{-1}$ $cm^{-1}$, at 280 nm).
Ext. coefficient    93085
Abs 0.1% (=1 g/l)   1.211, assuming ALL Cys residues appear as half cystines
Ext. coefficient    92710

Figure 1B

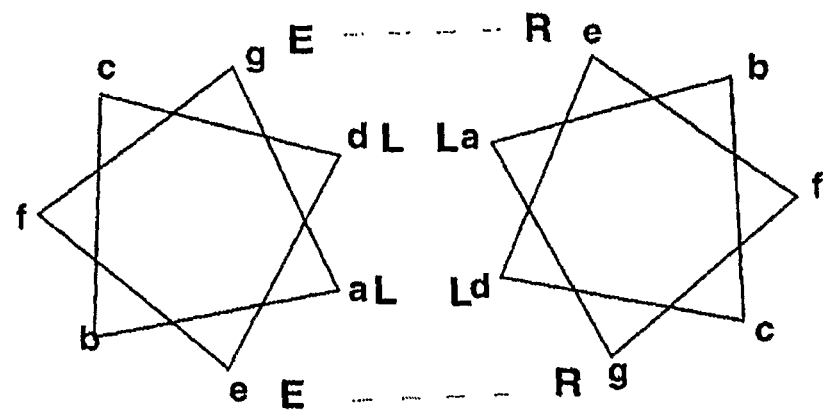
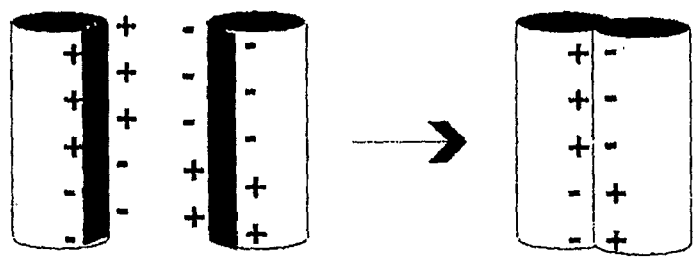
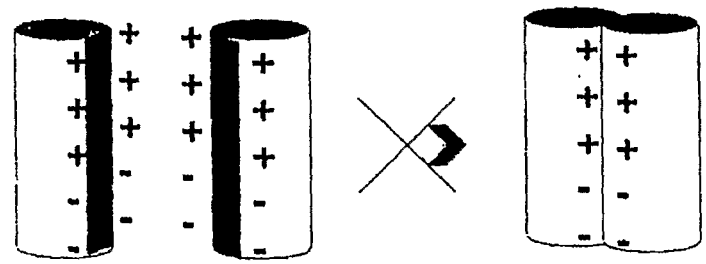
Figure 15

A

Enhanced FACS -
one colour for two markers

B Enhanced FACS - one color for two markers

| Cell Type | Demibody Specificity | Reconstituted Fc-Domain | Detected by |
|---|---|---|---|
| CD4+ TC | CD4<br>CD3 | Ig1 | anti-Ig1-green |
| CD8+ TC | CD8<br>CD3 | Ig2a | anti-Ig2a-red |
| Monocyte | CD14<br>Class II | IgM | anti-IgM-yellow |
| Dendritic Cell | CD83<br>Class II | IgD | anti-IgD-blue |

SEQUENCE LISTING

```
<160> NUMBER OF SEQ ID NOS: 10

<210> SEQ ID NO 1
<211> LENGTH: 47
<212> TYPE: PRT
<213> ORGANISM: Artificial sequence
<220> FEATURE:
<223> OTHER INFORMATION: Synthetic peptide

<400> SEQUENCE: 1

Leu Glu Ile Glu Ala Ala Phe Leu Glu Gln Glu Asn Thr Ala Leu Glu
1               5                   10                  15

Thr Glu Val Ala Glu Leu Glu Gln Glu Val Gln Arg Leu Glu Asn Glu
            20                  25                  30
```

```
Val Ser Gln Tyr Glu Thr Arg Tyr Gly Pro Leu Gly Gly Gly Lys
        35                  40                  45

<210> SEQ ID NO 2
<211> LENGTH: 47
<212> TYPE: PRT
<213> ORGANISM: Artificial sequence
<220> FEATURE:
<223> OTHER INFORMATION: Synthetic peptide

<400> SEQUENCE: 2

Lys Gly Gly Gly Leu Glu Ile Arg Ala Ala Phe Leu Arg Arg Asn
1               5                   10                  15

Thr Ala Leu Arg Thr Arg Val Ala Glu Leu Arg Gln Arg Val Gln Arg
            20                  25                  30

Ala Arg Asn Arg Val Ser Gln Tyr Arg Thr Arg Tyr Gly Pro Leu
        35                  40                  45

<210> SEQ ID NO 3
<211> LENGTH: 47
<212> TYPE: PRT
<213> ORGANISM: Artificial sequence
<220> FEATURE:
<223> OTHER INFORMATION: Synthetic peptide

<400> SEQUENCE: 3

Leu Glu Ile Arg Ala Ala Phe Leu Arg Gln Arg Asn Thr Ala Leu Arg
1               5                   10                  15

Thr Glu Val Ala Glu Leu Glu Gln Gly Val Gln Arg Leu Glu Asn Glu
            20                  25                  30

Val Ser Gln Tyr Glu Thr Arg Tyr Gly Pro Leu Gly Gly Gly Lys
        35                  40                  45

<210> SEQ ID NO 4
<211> LENGTH: 47
<212> TYPE: PRT
<213> ORGANISM: Artificial sequence
<220> FEATURE:
<223> OTHER INFORMATION: Synthetic peptide

<400> SEQUENCE: 4

Lys Gly Gly Gly Leu Glu Ile Glu Ala Ala Phe Leu Glu Arg Glu Asn
1               5                   10                  15

Thr Ala Leu Glu Thr Arg Val Ala Glu Leu Arg Gln Arg Val Gln Arg
            20                  25                  30

Ala Arg Asn Arg Val Ser Gln Tyr Arg Thr Arg Tyr Gly Pro Leu
        35                  40                  45

<210> SEQ ID NO 5
<211> LENGTH: 47
<212> TYPE: PRT
<213> ORGANISM: Artificial sequence
<220> FEATURE:
<223> OTHER INFORMATION: Synthetic peptide

<400> SEQUENCE: 5

Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Leu Arg Asn Arg
            20                  25                  30

Val Ser Gln Tyr Arg Thr Arg Tyr Gly Pro Leu Gly Gly Gly Lys
        35                  40                  45
```

<210> SEQ ID NO 6
<211> LENGTH: 1722
<212> TYPE: DNA
<213> ORGANISM: Artificial Sequence
<220> FEATURE:
<223> OTHER INFORMATION: Synthetic polynucleotide

<400> SEQUENCE: 6

```
ggtaccgatg atgatgataa acaggtgcag ctggttgaaa gcggcggtgg tctggttcag      60
ccgggtggct ctctgaaact gagctgcgcg gcgtctggct ttgattttag tcgttattgg     120
atgagctggg ttcgtcaggc accgggtaaa ggcctggaat ggattggcga aattaatccg     180
acgagtagca ccattaattt taccccgagc ctgaaagata aagtgttcat tagccgtgat     240
aacgcgaaaa acaccctgta cctgcagatg agtaaagttc gcagcgaaga taccgccctg     300
tattattgcg cacgtggtaa ctattaccgt tacggcgatg ccatggatta ttggggtcag     360
ggcaccagtg ttaccgttag caaaattagc ggcggcggtg gtagcggtgg cggtggcagc     420
ggcggtggcg gcagcggtgg tggcggtagc ggcggcggtg gttctagtga tatcgtgctg     480
acccagagtc cggcgagcct ggccgttttct ctgggtcagc gtgcaaccat cagctgccgc     540
gcgagcaaaa gtgtgagcac ctctggttat tcttatctgc attggtatca gcagaaaccg     600
ggccagccgc cgaaactgct gatttatctg gcgtctaatc tggaatctgg cgtgccggcg     660
cgcttcagcg gttctggcag tggcaccgat tttaccctga acattcatcc ggtggaagaa     720
gaagatgccg ccacctatta ctgccagcat agccgtgaac tgccgtttac ctttggcagc     780
ggtacgaaac tggaaatcaa agtcgacggt ggtggtggtt ctggtggtgg tggtagcggt     840
ggcggtggta gcggtggtgg cagatctatg gtcagcaaag gcgaagaaaa caacatggca     900
atcatcaaag aatttatgcg ttttaaagtt cgcatggaag gcagcgttaa cggccatgag     960
tttgaaatcg aaggcgaagg tgaaggccgt ccttatgaag cttccagacc tgctaaactg    1020
aaagtcacaa aaggcggtcc gctgcctttt gcatgggata ttctgagccc tcaatttaca    1080
tacggcagca agcgtatgt taaacatccg gctgatatcc ctgattattt taagctgtct    1140
tttccggaag ctttaagtg ggaacgtgtg atgaacttcg aagatggggg ggttgtgacc    1200
gtgacccagg attcatctct gcaggatgga gaatttattt ataaggtaaa actgcgtggc    1260
acgaatttcc ctagcgatgg cccagtgatg cagaaaaaga ccatgggttg ggaagctagc    1320
tctgaacgta tgtatccgga ggatggcgct ctgaaaggcg agatcaaaat gcgtctgaaa    1380
ctgaaagatg gtggccacta tgacgtccgaa gtaaaaacga cctacaaagc aaaaaagccg    1440
gttcagctgc cgggtgcgta tattgtcggg attaaactgg atattacaag ccataatgaa    1500
gattatacga ttgtggagca atatgaacgt gcggaaggcc gccacagtac gggtggtatg    1560
gatgaactgt acaaactcga gggtggtggt ggtagcggtg gtggtggttc tggtggtggc    1620
ggtagcggtg gcggtactag tgaaattagc gccctggaaa aagaaatcag cgcgctggaa    1680
aaagaaatta gcgcgctgga aaagcgagc taataagaat tc                        1722
```

<210> SEQ ID NO 7
<211> LENGTH: 1719
<212> TYPE: DNA
<213> ORGANISM: Artificial Sequence
<220> FEATURE:
<223> OTHER INFORMATION: Synthetic polynucleotide

<400> SEQUENCE: 7

```
ggtaccgacg acgacgacaa gatggatgtg gtgatgaccc agaccccggc gagcctgagc      60
gcgagcgtgg gcgaaaccgt gaccattacc tgccgtgcga gcggcagcat tcataactat     120
```

```
ctggcgtggt atcagcagaa actgggtaaa agcccgcagc tgctggtgta taacgcgaaa      180
accctggcgg atggtgtgcc gagccgtttt agcggcagcg gcagcggcac ccagtttagc      240
ctgaaaatta acagcctgca gccggaagat tttggcagct attattgcca gcattttggg      300
agcattccgt ggacctttgg tggtggcacc aaactggaac tgaaacgtgg tggcggtggt      360
ggcggcggtg gtagcggtgg cggcggcagc ggtggcggtg cagccaggt gcagctgcag      420 cagagcggca ccgaactggt gaaaccggtg gcgagcgtga aaatgagctg caaagcgagc      480
ggctttacct ttaccgatta taatatgcat tgggtgaaac agaccccggg tcagggcctg      540
gaatggattg cgcgattta tccggaaaac ggcgatacca gctataacca gcgctttaaa      600
ggcaaagcga ccctgaccgc ggataaaagc tttagcaccg cgtatatgca tctgagcagc      660
ctgaccagcg aagataccgc ggtgtatttt tgcgcgcgtt tttattatta tggcagctat      720
tatggcgcgc tggattattg gggccagggc accagcgtga ccgtgagcag cgatagcggc      780
gcggaatttg aagtcgacgg tggtggcggt tctggtggtg gtggtagcgg tggtggtggt      840
agcggcggtg gtagatctat gagcaaaggc gaagaactgt ttaccggcgt tgttccgatc      900
ctggtggaac tggatggcga tgtgaatggc cataaattta gcgttagcgg cgaaggcgaa      960
ggcgatgcca cctatggcaa actgaccctg aaattcattt gcaccaccgg taaactgccg     1020
gtgccgtggc cgaccctggt gaccaccttt agctatggtg tgatggtgtt tagccgttat     1080
ccggatcata tgaaacagca tgatttcttt aaaagcgcga tgccggaagg ctatgtgcag     1140
gaacgtacca ttttctttaa agatgatggc aattataaaa cccgtgcgga agtgaaatttt    1200 gaaggtgata ccctggtgaa ccgcattgaa ctgaaaggca ttgattttaa agaagatggt     1260
aatatcctgg gccacaaact ggaatataat tataatagcc ataatgtgta tattatggcg     1320
gataaacaga aaatggcat caaagcgaac ttcaaaattc gccataatat tgaagatggt     1380
ggtgtgcagc tggcggatca ttatcagcag aatacccga ttggcgatgg cccggttctg     1440
ctgccggata accattatct gagcattcag agcgcgctga gcaaagatcc gaatgaaaaa     1500
cgtgatcaca tggttctgct ggaatttgtg accgcggcgg gtatcaccca tggtatggat     1560
gaactgtata aactcgaggg tggtggtggt tctggtggtg gtggtagcgg cggcggtggt     1620
agcggtggtg gtactagtaa aattagcgcg ctgaaagaaa aattagcgc cctgaaagaa     1680 aaaatcagcg cgctgaaaga agcgagctaa taagaattc                           1719
```

<210> SEQ ID NO 8
<211> LENGTH: 18
<212> TYPE: PRT
<213> ORGANISM: Artificial Sequence
<220> FEATURE:
<223> OTHER INFORMATION: Synthetic peptide

<400> SEQUENCE: 8

Gly Gly Gly Gly Ser Gly Gly Gly Gly Ser Gly Gly Gly Gly Ser Gly
1               5                   10                  15

Gly Gly

<210> SEQ ID NO 9
<211> LENGTH: 721
<212> TYPE: PRT
<213> ORGANISM: Artificial sequence
<220> FEATURE:
<223> OTHER INFORMATION: Synthetic peptide

<400> SEQUENCE: 9

-continued

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
                35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
                100                 105                 110

Ser Gly His Met His His His His His His Ser Ser Gly Leu Val Pro
            115                 120                 125

Arg Gly Ser Gly Met Lys Glu Thr Ala Ala Ala Lys Phe Glu Arg Gln
        130                 135                 140

His Met Asp Ser Pro Asp Leu Gly Thr Asp Asp Asp Asp Lys Gln Val
145                 150                 155                 160

Gln Leu Val Glu Ser Gly Gly Gly Leu Val Gln Pro Gly Gly Ser Leu
                165                 170                 175

Lys Leu Ser Cys Ala Ala Ser Gly Phe Asp Phe Ser Arg Tyr Trp Met
                180                 185                 190

Ser Trp Val Arg Gln Ala Pro Gly Lys Gly Leu Glu Trp Ile Gly Glu
        195                 200                 205

Ile Asn Pro Thr Ser Ser Thr Ile Asn Phe Thr Pro Ser Leu Lys Asp
210                 215                 220

Lys Val Phe Ile Ser Arg Asp Asn Ala Lys Asn Thr Leu Tyr Leu Gln
225                 230                 235                 240

Met Ser Lys Val Arg Ser Glu Asp Thr Ala Leu Tyr Tyr Cys Ala Arg
                245                 250                 255

Gly Asn Tyr Tyr Arg Tyr Gly Asp Ala Met Asp Tyr Trp Gly Gln Gly
            260                 265                 270

Thr Ser Val Thr Val Ser Lys Ile Ser Gly Gly Gly Ser Gly Gly Gly
        275                 280                 285

Gly Gly Ser Gly Gly Gly Ser Gly Gly Gly Ser Gly Gly Gly
    290                 295                 300

Gly Ser Ser Asp Ile Val Leu Thr Gln Ser Pro Ala Ser Leu Ala Val
305                 310                 315                 320

Ser Leu Gly Gln Arg Ala Thr Ile Ser Cys Arg Ala Ser Lys Ser Val
            325                 330                 335

Ser Thr Ser Gly Tyr Ser Tyr Leu His Trp Tyr Gln Gln Lys Pro Gly
            340                 345                 350

Gln Pro Pro Lys Leu Leu Ile Tyr Leu Ala Ser Asn Leu Glu Ser Gly
        355                 360                 365

Val Pro Ala Arg Phe Ser Gly Ser Gly Ser Gly Thr Asp Phe Thr Leu
370                 375                 380

Asn Ile His Pro Val Glu Glu Glu Asp Ala Ala Thr Tyr Tyr Cys Gln
385                 390                 395                 400

His Ser Arg Glu Leu Pro Phe Thr Phe Gly Ser Gly Thr Lys Leu Glu
                405                 410                 415

Ile Lys Val Asp Gly Gly Gly Gly Ser Gly Gly Gly Gly Ser Gly Gly
            420                 425                 430
```

-continued

```
Gly Gly Ser Gly Gly Arg Ser Met Val Ser Lys Gly Glu Glu Asn
        435                 440                 445

Asn Met Ala Ile Ile Lys Glu Phe Met Arg Phe Lys Val Arg Met Glu
450                 455                 460

Gly Ser Val Asn Gly His Glu Phe Glu Ile Glu Gly Glu Gly Glu Gly
465                 470                 475                 480

Arg Pro Tyr Glu Gly Phe Gln Thr Ala Lys Leu Lys Val Thr Lys Gly
                485                 490                 495

Gly Pro Leu Pro Phe Ala Trp Asp Ile Leu Ser Pro Gln Phe Thr Tyr
            500                 505                 510

Gly Ser Lys Ala Tyr Val Lys His Pro Ala Asp Ile Pro Asp Tyr Phe
        515                 520                 525

Lys Leu Ser Phe Pro Glu Gly Phe Lys Trp Glu Arg Val Met Asn Phe
    530                 535                 540

Glu Asp Gly Gly Val Val Thr Val Thr Gln Asp Ser Ser Leu Gln Asp
545                 550                 555                 560

Gly Glu Phe Ile Tyr Lys Val Lys Leu Arg Gly Thr Asn Phe Pro Ser
                565                 570                 575

Asp Gly Pro Val Met Gln Lys Lys Thr Met Gly Trp Glu Ala Ser Ser
            580                 585                 590

Glu Arg Met Tyr Pro Glu Asp Gly Ala Leu Lys Gly Glu Ile Lys Met
        595                 600                 605

Arg Leu Lys Leu Lys Asp Gly Gly His Tyr Thr Ser Glu Val Lys Thr
    610                 615                 620

Thr Tyr Lys Ala Lys Lys Pro Val Gln Leu Pro Gly Ala Tyr Ile Val
625                 630                 635                 640

Gly Ile Lys Leu Asp Ile Thr Ser His Asn Glu Asp Tyr Thr Ile Val
                645                 650                 655

Glu Gln Tyr Glu Arg Ala Glu Gly Arg His Ser Thr Gly Gly Met Asp
            660                 665                 670

Glu Leu Tyr Lys Leu Glu Gly Gly Gly Ser Gly Gly Gly Gly Ser
        675                 680                 685

Gly Gly Gly Ser Gly Gly Gly Thr Ser Glu Ile Ser Ala Leu Glu
    690                 695                 700

Lys Glu Ile Ser Ala Leu Glu Lys Glu Ile Ser Ala Leu Glu Lys Ala
705                 710                 715                 720

Ser
```

<210> SEQ ID NO 10
<211> LENGTH: 720
<212> TYPE: PRT
<213> ORGANISM: Artificial sequence
<220> FEATURE:
<223> OTHER INFORMATION: Synthetic peptide

<400> SEQUENCE: 10

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
```

```
                65                  70                  75                  80
Leu Phe Lys Asn Gly Glu Val Ala Ala Thr Lys Val Gly Ala Leu Ser
                        85                  90                  95
Lys Gly Gln Leu Lys Glu Phe Leu Asp Ala Asn Leu Ala Gly Ser Gly
                100                 105                 110
Ser Gly His Met His His His His His His Ser Ser Gly Leu Val Pro
                115                 120                 125
Arg Gly Ser Gly Met Lys Glu Thr Ala Ala Ala Lys Phe Glu Arg Gln
                130                 135                 140
His Met Asp Ser Pro Asp Leu Gly Thr Asp Asp Asp Lys Met Asp
145                 150                 155                 160
Val Val Met Thr Gln Thr Pro Ala Ser Leu Ser Ala Ser Val Gly Glu
                165                 170                 175
Thr Val Thr Ile Thr Cys Arg Ala Ser Gly Ser Ile His Asn Tyr Leu
                180                 185                 190
Ala Trp Tyr Gln Gln Lys Leu Gly Lys Ser Pro Gln Leu Leu Val Tyr
                195                 200                 205
Asn Ala Lys Thr Leu Ala Asp Gly Val Pro Ser Arg Phe Ser Gly Ser
                210                 215                 220
Gly Ser Gly Thr Gln Phe Ser Leu Lys Ile Asn Ser Leu Gln Pro Glu
225                 230                 235                 240
Asp Phe Gly Ser Tyr Tyr Cys Gln His Phe Trp Ser Ile Pro Trp Thr
                245                 250                 255
Phe Gly Gly Gly Thr Lys Leu Glu Leu Lys Arg Gly Gly Gly Gly
                260                 265                 270
Gly Gly Gly Ser Gly Gly Gly Ser Gly Gly Gly Ser Gln Val
                275                 280                 285
Gln Leu Gln Gln Ser Gly Thr Glu Leu Val Lys Pro Val Ala Ser Val
                290                 295                 300
Lys Met Ser Cys Lys Ala Ser Gly Phe Thr Phe Thr Asp Tyr Asn Met
305                 310                 315                 320
His Trp Val Lys Gln Thr Pro Gly Gln Gly Leu Glu Trp Ile Gly Ala
                325                 330                 335
Ile Tyr Pro Glu Asn Gly Asp Thr Ser Tyr Asn Gln Arg Phe Lys Gly
                340                 345                 350
Lys Ala Thr Leu Thr Ala Asp Lys Ser Phe Ser Thr Ala Tyr Met His
                355                 360                 365
Leu Ser Ser Leu Thr Ser Glu Asp Thr Ala Val Tyr Phe Cys Ala Arg
                370                 375                 380
Phe Tyr Tyr Tyr Gly Ser Tyr Tyr Gly Ala Leu Asp Tyr Trp Gly Gln
385                 390                 395                 400
Gly Thr Ser Val Thr Val Ser Ser Asp Ser Gly Ala Glu Phe Glu Val
                405                 410                 415
Asp Gly Gly Gly Gly Ser Gly Gly Gly Ser Gly Gly Gly Ser
                420                 425                 430
Gly Gly Gly Arg Ser Met Ser Lys Gly Glu Glu Leu Phe Thr Gly Val
                435                 440                 445
Val Pro Ile Leu Val Glu Leu Asp Gly Asp Val Asn Gly His Lys Phe
                450                 455                 460
Ser Val Ser Gly Glu Gly Glu Gly Asp Ala Thr Tyr Gly Lys Leu Thr
465                 470                 475                 480
Leu Lys Phe Ile Cys Thr Thr Gly Lys Leu Pro Val Pro Trp Pro Thr
                485                 490                 495
```

```
Leu Val Thr Thr Phe Ser Tyr Gly Val Met Val Phe Ser Arg Tyr Pro
            500             505             510

Asp His Met Lys Gln His Asp Phe Phe Lys Ser Ala Met Pro Glu Gly
            515             520             525

Tyr Val Gln Glu Arg Thr Ile Phe Phe Lys Asp Asp Gly Asn Tyr Lys
            530             535             540

Thr Arg Ala Glu Val Lys Phe Glu Gly Asp Thr Leu Val Asn Arg Ile
545             550             555             560

Glu Leu Lys Gly Ile Asp Phe Lys Glu Asp Gly Asn Ile Leu Gly His
                565             570             575

Lys Leu Glu Tyr Asn Tyr Asn Ser His Asn Val Tyr Ile Met Ala Asp
            580             585             590

Lys Gln Lys Asn Gly Ile Lys Ala Asn Phe Lys Ile Arg His Asn Ile
            595             600             605

Glu Asp Gly Gly Val Gln Leu Ala Asp His Tyr Gln Gln Asn Thr Pro
            610             615             620

Ile Gly Asp Gly Pro Val Leu Leu Pro Asp Asn His Tyr Leu Ser Ile
625             630             635             640

Gln Ser Ala Leu Ser Lys Asp Pro Asn Glu Lys Arg Asp His Met Val
            645             650             655

Leu Leu Glu Phe Val Thr Ala Ala Gly Ile Thr His Gly Met Asp Glu
            660             665             670

Leu Tyr Lys Leu Glu Gly Gly Gly Ser Gly Gly Gly Gly Ser Gly
            675             680             685

Gly Gly Gly Ser Gly Gly Gly Thr Ser Lys Ile Ser Ala Leu Lys Glu
            690             695             700

Lys Ile Ser Ala Leu Lys Glu Lys Ile Ser Ala Leu Lys Glu Ala Ser
705             710             715             720
```

DEMIBODIES: DIMERIZATION-ACTIVATED THERAPEUTIC AGENTS

This application is U.S. National Phase of International Application PCT/AU2006/001810, filed Nov. 29, 2006, designating the U.S., and published in English as WO 2007/062466 on Jun. 7, 2007, which claims priority to Australian Patent Application No. 2006901059, filed Mar. 2, 2006 and U.S. Provisional Application No. 60/741,030, filed Nov. 29, 2005.

BACKGROUND OF THE INVENTION

1. Field of the Invention

The present invention relates generally to a set of synthetic immunointeractive molecules referred to herein as "demibodies" which are useful in targeting particular cells in a subject. More particularly, the present invention provides a set of demibodies wherein at least two molecules from within the set, each specific for a different antigen on a target cell, are required to interact together at the cell surface in order to form an active complex which directs demibody-mediated cellular or complement mediated cytotoxicity and/or reporter function and/or therapeutic activity. The demibodies of the present invention are useful in the targeting of particular cells such as cancer cells including leukemic cells, pathogens including malarial, bacterial and viral agents, and stem cells including embryonic and adult stem cells and pathogen cells. The present invention provides, therefore, methods of treatment, diagnosis and undertaking research and compositions comprising demibodies useful for same.

2. Description of the Prior Art

Bibliographic details of the publications referred to by author in this specification are collected at the end of the description.

Reference to any prior art in this specification is not, and should not be taken as, an acknowledgment or any form of suggestion that this prior art forms part of the common general knowledge in any country.

A key feature in the search for and development of therapeutic agents is target discrimination or selective toxicity. In particular, the ability to distinguish target cells such as cancer cells or cells infected with pathogen cells amongst a population of normal cells in a subject is of paramount importance. This is particularly the case in cancer therapies where the target cancer cells have many physiological, anatomical and biochemical properties in common with surrounding normal cells. Whilst some anti-cancer drugs do cause collateral damage to normal cells, their use may be indicated or at least justified for particularly aggressive, fast growing cancers.

Therapeutic antibodies are the most rapidly growing area of pharmaceuticals, with more than 30 antibodies in late-phase clinical trials (Hudson and Souriau, *Nat Med* 9:129-134, 2003). There are many variations of engineered antibodies (e.g. mouse monoclonal, chimeric, humanized, human monoclonal, single chain variable antibody fragments (scFv), minibodies, aptamers). Diabodies developed using recombinant DNA technology, contain two or more single chain variable antibody fragments (scFv) with different binding specificities and appropriate spacing between these domains to enable both scFv to bind antigens concurrently (Hudson and Souriau, supra 2003). Bivalent and bispecific scFv antibodies have been formed using leucine zipper-based dimerization cassettes attached to different scFv (de Kruif and Logtenberg, *J Biol Chem* 271:7630-7634, 1996). Bi-specific antibodies with different scFv domains connected by a polypeptide chain have been designed to cross-link T-cells with tumours. The two or more interactions that such chimeric antibodies have with different surface antigens on a cell would greatly increase the strength of binding since the dissociation constants for the individual interactions are multiplicative.

Whilst therapeutic antibodies are, important, multi-specific antibodies have not been as successful. There is a need, therefore, to develop antibody-based drugs and other therapeutic agents which are more highly selective for target cells.

Whole antibodies have been proposed as highly specific targeting agents (Carter, *Nature Reviews* 1:118-128, 2001). In one proposal, cytotoxic agents are linked to an antibody specific for an antigen on a target cell. However, although antibodies have a high degree of target specificity, they have not achieved wide pathological therapeutic use and are primarily used in clinical imaging applications. This may be due to their relatively long circulating half-lives and their associated effector functions.

Modified antibodies, however, have achieved some level of acceptance in immuno-therapeutic applications (Carter (2001) supra; de Haard et al, *Adv. Drug Delivery Rev.* 31.5-31, 1998; Chames and Baty, *FEMS Microbiol. Lett.* 189:1-8, 2000; Funaro et al, *Biotechnol. Adv.* 18:385-401, 2000; Hudson, *Exp. Opin. Invest Drugs* 9.1231-1242, 2000).

Examples involving therapeutic antibodies are reviewed in Table 1 of Carter (2001) supra.

These antibodies all contain the Fc domain which is required for complement-dependent cytotoxicity (CDC) and antibody-dependent cellular cytotoxicity (ADCC).

Another useful development in the use of antibody fragments is their fusion to active agents such as radioactive isotypes (Wu et al, *Immunotechnology* 2:21-36, 1996; Wu et al, *Proc. Natl. Acad. Sci. USA* 97:8495-8500, 2000; Adams et al, *Nuc. Med. Biol.* 27:330-346, 2000), enzymes for producing therapy (Bagshawe and Begent, *Adv. Drug Delivery Rev.* 22:365-367, 1996) and toxins for targeted cell killing (Reiter and Pastan, *Tibtech* 16:51-520, 1998; Kreitman, *Curr. Opin. Immunol.* 11:570-578, 1999).

Modified antibodies of particular interest are single chain variable fragments (scFv) carrying the variable region sequences of the light and heavy chains linked together. scFv antibody fragments are derived from Fragment antigen binding (Fab) portions of an antibody comprising the V region of a heavy chain linked by a stretch of synthetic peptide to a V region of a light chain.

Whilst scFv antibody fragments have achieved a reasonable level of utility as targeting molecules, they lack the Fc domain and are unable to induce ADCC or CDC.

The present invention enables modified forms of scFv antibody fragments to be used in targeted cell therapy and/or diagnosis and/or research.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The present invention combines the specificity of antibody-antigen interactions to generate immunointeractive molecules referred to herein as "demibodies" which are capable of targeting particular cells and inducing cytotoxicity and/or reporter function and/or facilitating cell therapy. More particularly, one aspect of the present invention provides sets of at least two demibodies wherein each demibody comprises an antigen-binding portion, an agent or portion thereof and one or other member of a binding pair. Two demibodies are designed such that when in close proximity, each member constituting one of a complementary binding pair, interacts forming a binding pair. This in turn permits interaction of portions of the agent to generate a functional agent or interaction of two agents which agent or agents have properties resulting in for example, cell death, cell therapy or providing a reporter signal. Hence, the agent on the demibodies can act as or form a reporter molecule, therapeutic molecule or cytotoxic molecule. Preferably, the demibodies comprise non-functional portions of the agent. When in close proximity, the reporter or therapeutic or cytotoxic molecule portions come together and a functional molecule capable of providing a signal or inducing cytotherapy or cytotoxicity is reconstituted. This increases the specificity for imaging, diagnostic and therapeutic purposes. The demibodies are also useful research tools such as for FACS, Flow cytometry and affinity chromatography. The demibodies may also be used to detect products of cells such as proteins or different phosphorylated or glycosylated or other post-translational modifications thereof. In essence, the demibodies of the present invention enable enhanced immunophenotypic selection of cells, viruses or products thereof such as proteins.

The antigen binding portion may be derived from an immunoglobulin such as a scFv (or F'ab fragment) or any affinity scaffold such as a microaffinity scaffold. Examples include dAbs, nanobodies, microproteins, fibronectins, microbodies, anticalins, aptamers, darpins, avimers, afflins, and Kunitz domains.

The demibodies have enhanced target specificity since each demibody in the set is specific for a particular antigen. Hence, by selecting cells or virus having an unusual pair of antigens reduces the risk of non-specific binding.

In one embodiment, each demibody carries an incomplete Fc domain but upon binding of the pair of demibodies, the two incomplete Fc domains now form a functional Fc domain or functional portion thereof. The bound demibodies together have a biologically functional Fc domain and can initiate associated activities such as antibody-dependent cellular cytotoxicity (ADCC) and/or complement-dependent cytotoxicity (CDC). In another embodiment, the two incomplete domains form, when reconstituted, an agent such as a reporter molecule, therapeutic agent or cytotoxic agent. In a further embodiment, the agents are dyes such as fluorchromes which when together provide a particular signal.

Hence, one aspect of the present invention provides a composition comprising a set of pairs of demibodies which, together, are able to induce highly selective cytotoxicity. The selective toxicity follows the demibodies interacting with at least two different antigens on the surface of a target cell. The two different antigens being predominantly only expressed simultaneously on a target cell population. Even if one of these antigens (or analogous antigens) is represented on normal cells, unless both antigens are present on the one cell, the pair of demibodies will not come together on the surface of the cell via the complementary binding pairs to form a functional cytotoxic domain such as a functional Fc domain, therapeutic molecule, cytotoxic molecule or reporter molecule.

In a further embodiment, the reconstitution of the demibody pairs results in a functional cytotoxic or therapeutic molecule. Examples of such reconstituted functional molecules are apoptotic, cell cycle static, lytic or cytotoxic molecules, antibiotics, peptides and cytokines.

In an alternative embodiment, each demibody carries a functional reporter molecule such as a dye or fluorescent marker and when the demibodies reconstitute together, the combined signal (or combined dye) or combined fluorescent signal is different from the individual signals (or dyes). Examples of fluorescent markers include hydroxycoumarin, aminocoumarin, methoxycumarin, cascade blue, Lucifer yellow, NBD, Phycoerythrin (PE), PerCP, allophycocyanin, hoechst 33342, DAP1, SYTOX Blue, hoechst 33258, chromomycin A3, mithramycin, YOYO-1, SYTOX green, SYTOX orange, 7-AAD, acridine orange, TOTO-1, To-PRO-1, thiazole orange, TOTO-3, TO-PRO-3, LDS 751, Alexa Fluor dyes including Alexa Fluoro-350, -430, -488, -532, -546, -555, -556, -594, -633, -647, -660, -680, -700 and -750; BoDipy dyes, including BoDipy 630/650 and BoDipy 650/665; CY dyes, particularly Cy2, Cy3, Cy3.5, Cy5; Cy 5.5 and Cy7; 6-FAM (Fluorescein); PE-Cy5, PE-Cy7, Fluorescein dT; Hexachlorofluorescein (Hex); 6-carboxy-4',5'-dichloro-2',7'-dimethoxyfluorescein (JOE); Oregon green dyes, including 488-X and 514; Rhodamine dyes, including X-Rhodamine, Lissamine Rhodamine B, Rhodamine Green, Rhodamine Red and ROX; TRITC, Tetramethylrhodamine (TMR); Carboxytetramethylrhodamine (TAMRA); Tetrachlorofluorescein (TET); Red 6B, Fluor X, BODIPY-FL and Texas Red.

The demibodies of the present invention are useful in the treatment of a range of conditions including cancer, infection by pathogenic agents or the selective targeting of any cell type in a subject. They are also useful in targeting cells such as stem cells.

Reference to a subject includes a human or other primate, livestock animal, laboratory test animal, companion animal or avian species. A subject may also be regarded as a patient.

The present invention contemplates, therefore, a method of treating in a subject, such as a patient, comprising administering to the subject at least two demibodies which, when bound together via binding pairs, forms a functional cytotoxic domain such as an Fc domain or functional portion thereof capable of inducing cell cytotoxicity such as ADCC or CDC. Alternatively, the demibodies reconstitute a cytotoxic agent or therapeutic molecule.

Diagnostic compositions and methods for diagnosing and/or imaging and/or therapy also form part of the present invention.

The pair of immunointeractive molecules may be simultaneously or sequentially administered.

The present invention further provides a method for selectively identifying a cell said method comprising contacting said cell with a pair of demibodies wherein each demibody comprises first, second and third portions wherein said first portions are capable of interacting with one or two antigens on the cell, said second portions comprise distinct reporter molecules or complementary non-functional portions of a single reporter molecule and said third portions are complementary binding pairs wherein upon binding of the individual demibodies to the two antigens, the binding pairs combine enabling the reporter molecules to provide a combined signal or to reconstitute a single reporter molecule.

A list of abbreviations used herein is provided in Table 1.

TABLE 1

Abbreviations

| ABBREVIATION | DESCRIPTION |
|---|---|
| Ab | antibody |
| ADCC | antibody-dependent cellular cytotoxicity |
| Ag | antigen |
| C region | constant region |
| CD antigen | cluster of differentiation antigen |

TABLE 1-continued

Abbreviations

| ABBREVIATION | DESCRIPTION |
| --- | --- |
| CDC | complement-dependent cytotoxicity |
| Fab fragment | fragment antigen binding |
| Fc | fragment crystalline |
| FcR | Fc receptor |
| Fv | fragment variable |
| H chain | heavy chain |
| Ig | immunoglobulin |
| L chain | light chain |
| sc | single chain |
| scFv | single chain variable fragment, recombinant Fab comprising V region of heavy and light chains |
| V region | variable region |

BRIEF DESCRIPTION OF THE FIGURES

FIGS. 1A and B are a representations of the amino acid sequences for the thioredoxin-Demibody conjugates. (A) Trx-CD45-mOrange-E3 (Demibody A, DBA; SEQ ID NO: 9) and (B) Trx-CD20-T-Sapphire-K3 (Demibody B5 DBB5; SEQ ID NO: 10).

FIG. 15 is a diagrammatic representation showing leucine zipper heterodimerization. Top: helical wheel representation (looking down long axis of helices) of heterodimerization. Bottom: schematic showing that complementary electrostatic charges mediate heterodimerization not homodimerization.

DETAILED DESCRIPTION OF THE INVENTION

Figure 2A:
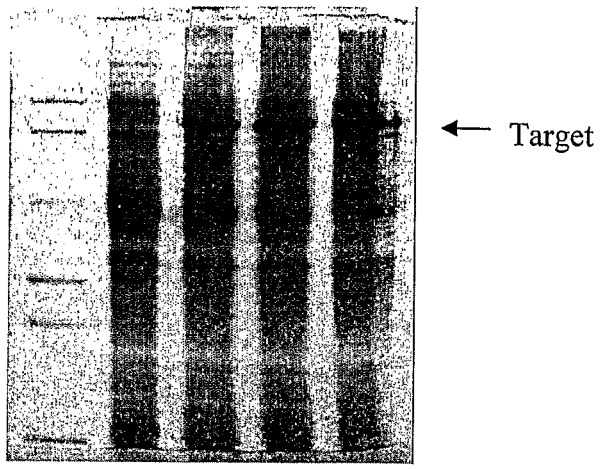
FIGS. 2A through 2D are photographic representations of protein gels. (A and B) Presence of ~78 kDa band (marked "target") from an induced sample showing an expression of pET32a-30103s1 and pET32a-30103s2, (C) The samples in (A) and (B) were purified by metal-affinity chromatography under denaturing conditions, refolded and run on SDS-PAGE, which showed ~80 purity. (D) Demonstration of the expression of Trx-DBA and His$^6$-GST-DBB in soluble fraction with ~50% soluble protein.
Figure 2B:
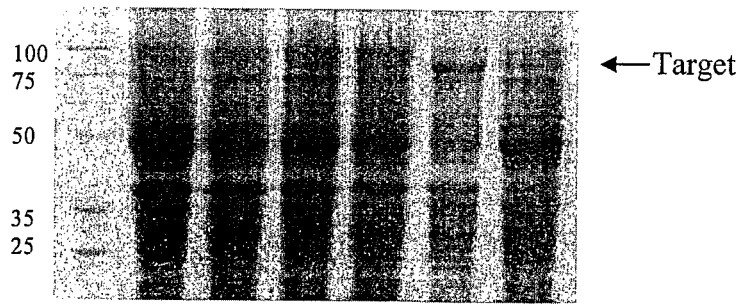

The present invention relates to a pair of modified immunoglobulin molecules which form an antibody-like immunointeractive molecule. The term "immunointeractive" in this context is used to highlight one of the principal features of an antibody, i.e. the ability for an antibody to interact specifically with an antigen. As each molecule is effectively half of an antibody-like molecule, it is referred to herein as a "demibody". The present invention encompasses, therefore, antibodies modified recombinantly and/or chemically to form a single chain variable fragment (e.g. scFv) having specificity to one antigen. Such demibodies may also be referred to herein as immunointeractive molecules or modified or chimeric immunoglobulins or modified or chimeric antibodies.

The demibodies of the present invention comprise:
(i) an scFv antigen binding portion;
(ii) an agent or non-function portion thereof; and
(iii) a member of a binding pair capable of interacting with a member on a second demibody, thereby forming a binding pair of heterodimers but not homodimers.

In use, at least two demibodies are selected having:
(i) scFv antigen binding portions directed to different antigens on a target cell;
(ii) an agent or non-functional portion thereof such that if both demibodies were bound together, a functional agent is formed; and
(iii) two binding members so that, in close proximity, both members can interact to form a binding pair between complementary partners.

In one embodiment, the incomplete non-functional portion of an agent is an Fc domain or a functional portion thereof. In this case, complementary, incomplete and non-functional Fc domains are used on each demibody. Alternatively, the non-functional portions are of a cytotoxic molecule or a reporter molecule or a therapeutic molecule. In still another embodiment, the agent is functional but when both agents are together, a particular result occurs (such as a signal) absent from one agent above.

Hence, the agent, when reconstituted, may have cytotoxic, medicament, therapeutic or reporter signal properties.

The demibodies have a range of applications including cytotoxic targeting of cancer cells or pathogens, selective detection of cells such as cancer cells, stem cells (embryonic or adult) or cells infected with pathogens. Cell detection may be facilitated with FACS, Flow cytometry and fluorescent microscopy. The demibodies also have research applications such as affinity chromatography. The demibodies may also be used to detect products of cells such as proteins or different phosphorylated or glycosylated or other post-translational modifications thereof. The detection of different forms of proteins is particularly useful for diagnosing or prognosing disease conditions or levels of health.

In relation to one embodiment, the formation of the binding pair results in the formation of a functional Fc domain or portion thereof. The Fc domain generally corresponds to paired $C_H2$ and $C_H3$ domains and is the part of an antibody which interacts with effector molecules and cells carrying Fc receptors. The coming together of the incomplete Fc domains to form a functional Fc domain means that a sufficient amount of Fc required to interact with effector molecules or Fc receptors on cells is formed. It may still represent an incomplete Fc domain. The present invention encompasses, therefore, the use of complete or incomplete Fc domains provided that the Fc domain is functional with respect to interacting with effector molecules or cells when two demibodies are bound together. Individual immunointeractive molecules have incomplete, non-functional Fc domains.

In a preferred embodiment, the incomplete, non-functional Fc domains correspond to the γ2a and γ2b chains. Each demibody, in a preferred embodiment, carries either a γ2a chain or a γ2b chain of the Fc domain.

It will be appreciated, therefore, that in operation, a set of at least two demibodies is required which are complementary with respect to Fc domains and binding members and which have antigen binding portions directed to different antigens, which antigens are co-expressed on a target cell.

Accordingly, one aspect of the present invention provides a demibody comprising first, second and third portions wherein:
said first portion is capable of interacting with a first antigen on a target cell;
said second portion is a non-functional, incomplete Fc domain; and
said third portion is one member of a complementary binding pair;
wherein said demibody is capable of forming a functional Fc domain when the demibody is bound to a second complementary demibody which comprises a portion which interacts with another antigen on said target cell.

The functional Fc domain is useful for mediating ADCC of target cells.

The present invention further provides a set of demibodies comprising a first demibody with first, second and third portions wherein:
said first portion is capable of interacting with a first antigen on a target cell;
said second portion is a non-functional, incomplete a Fc domain; and
said third portion is one member of a complementary binding pair; and
a second demibody comprising a first portion which is capable of interacting with a different antigen on said target cell;
a second portion which, in combination with the second portion of the first mentioned demibody forms a functional Fc domain; and
a third portion which is the complementary binding member of said binding pair.

The present invention further contemplates a method for selectively inducing cytotoxicity of a cell, said method comprising contacting cells with first and second demibodies wherein said first demibody comprises first, second and third portions wherein:
said first portion is capable of interacting with a first antigen on a target cell;
said second portion is a non-functional, incomplete Fc domain; and
said third portion is one member of a complementary binding pair; and
said second demibody comprises a first portion which is capable of interacting with a different antigen on said target cell;
a second portion which, in combination with the second portion of the first mentioned demibody forms a functional Fc domain; and
a third portion which is the complementary binding member of said binding pair;
said demibodies administered for a time and under conditions sufficient for a functional Fc-containing antibody to be reconstituted and to mediate lysis of said cell.

Although these aspects of the present invention relate to the Fc domain as the functional portion (i.e the agent), the subject invention extends to other cytotoxic domains such as apoptotic domains or lysing domains from agents inducing cell cycle arrest, and domains of therapeutic molecules.

As an alternative to the incomplete Fc domains, therefore, the present invention extends to incomplete domains for cytotoxic molecules, therapeutic molecules and reporter molecules.

Accordingly, another aspect of the present invention provides a demibody comprising first, second and third portions wherein:
said first portion is capable of interacting with a first antigen on a target cell;

said second portion is a non-functional, incomplete domain of cytotoxic or therapeutic or reporter molecule; and said third portion is one member of a complementary binding pair;

wherein said demibody is capable of forming a functional cytotoxic or therapeutic or reporter molecule when the demibody is bound to a second complementary demibody which comprises a first portion capable of interacting with another antigen on said target cell;

a second portion which, in combination with the second portion of the first mentioned demibody forms a functional Fc domain; and a third portion which is the complementary binding member of said binding pair.

The demibody is, in effect, a modular or chimeric molecule having first, second and third modules equivalent to the first, second and third portions defined above.

The present invention further provides a set of demibodies comprising a first demibody with first, second and third portions wherein:

said first portion is capable of interacting with a first antigen on a target cell;

said second portion is a non-functional, incomplete cytotoxic or therapeutic or reporter molecule; and said third portion is one member of a complementary binding pair; and a second demibody comprising a first portion which is capable of interacting with a different antigen on said target cell;

a second portion which, in combination with the second portion of the first mentioned demibody forms a functional cytotoxic or therapeutic or reporter molecule; and a third portion which is the complementary binding member of said binding pair.

The present invention further contemplates a method for selectively detecting or targeting a cell, said method comprising contacting cells with first and second demibodies wherein said first demibody comprises first, second and third portions wherein:

said first portion is capable of interacting with a first antigen on a target cell;

said second portion is a non-functional, incomplete a cytotoxic or therapeutic or reporter molecule; and said third portion is one member of a complementary binding pair; and said second demibody comprises a first portion which is capable of interacting with a different antigen on said target cell;

a second portion which, in combination with the second portion of the first mentioned demibody forms a functional cytotoxic or therapeutic or reporter molecule; and a third portion which is the complementary binding member of said binding pair.

In a further embodiment, each demibody carries a reporter molecule such as a dye which when the two demibodies reconstitute with each other, the combined reporter molecules (e.g. combined dyes) provide a distinctive signal. Examples of dyes include fluorescent dyes such as hydroxycoumarin, aminocoumarin, methoxycumarin, cascade blue, Lucifer yellow, NBD, Phyccerythrin (PE), PerCP, allophycocyanin, hoechst 33342, DAPI, SYTOX Blue, hoechst 33258, chromomycin A3, mithramycin, YOYO-1, SYTOX green, SYTOX orange, 7-AAD, acridine orange, TOTO-1, To-PRO-1, thiazole orange, TOTO-3, TO-PRO-3, LDS 751, Alexa Fluor dyes including Alexa Fluoro-350, -430, -488, -532, -546, -555, -556, -594, -633, -647, -660, -680, -700 and -750; BoDipy dyes, including BoDipy 630/650 and BoDipy 650/665; CY dyes, particularly Cy2, Cy3, Cy3.5, Cy5, Cy5.5 and Cy7; 6-FAM (Fluorescein); PE-Cy5, PE-Cy7, Fluorescein dT; Hexachlorofluorescein (Hex); 6-carboxy-4',5'-dichloro-2',7'-dimethoxyfluorescein (JOE); Oregon green dyes, including 488-X and 514; Rhodamine dyes, including X-Rhodamine, Lissamine Rhodamine B, Rhodamine Green, Rhodamine Red and ROX; TRITC, Tetramethylrhodamine (TMR); Carboxytetramethylrhodamine (TAMRA); Tetrachlorofluorescein (TET); Red 6B, Fluor X, BODIPY-FL and Texas Red.

The present invention further contemplates a method for selectively identifying a cell said method comprising contacting said cell with a pair of demibodies wherein each demibody comprises first, second and third, portions wherein said first portions are capable of interacting with one or two antigens on the cell, said second portions comprise distinct reporter molecules or complementary non-functional portions of a single reporter molecule and said third portions are complementary binding pairs wherein upon binding of the individual demibodies to the two antigens, the binding pairs combine enabling the reporter molecules to provide a combined signal or to reconstitute a single reporter molecule.

In the above aspects, the antigen binding portion may be derived from an immunoglobulin or may be any affinity scaffold such as but not limited to dAbs, nanobodies, microproteins, fibronectins, microbodies, anticalins, aptamers, darpins, avimers, afflins, and Kunitz domains.

Administration may be sequential or simultaneous. Sequential administration includes separate administration of both demibodies within nanoseconds, seconds, minutes, hours or days. Simultaneous administration includes co-administration in a single composition or in two separate compositions.

The subject may be a human or other primate, a livestock animal (e.g. sheep, cow, pig, horse, donkey, goat), laboratory test animal (e.g. mouse, rat, rabbit, guinea pig), captive wild animal or avian species (e.g. poultry birds, caged birds, aviary birds, game birds, captive wild birds). A subject may also be regarded as a patient.

The antigen-binding portion is generally a recombinant Fab fragment. This fragment corresponds to the arms of an antibody molecule which contains the complete light chains paired with the $V_H$ and $C_H$ domains of the heavy chains.

Generally, the antigen binding portion is an scFv portion of an antibody. scFv are generally monomeric although the extent of monomerism compared to dimerism or multivalentism may depend on the size of the linker between the $V_H$ and $V_L$ domains. The construction of scFv molecules is described in Hudson (1999) supra and Kortt et al, *Biomolecular Engineering* 18:95-108, 2001.

The present invention extends to other antigen binding portions of immunoglobulins such as but not limited to dAbs, nanobodies, microproteins, fibronectins, microbodies, anticalins, aptamers, darpins, avimers, afflins, and Kunitz domains or other affinity scaffolds such as but not limited to microscaffolds.

The antigen binding portion is specific for an antigen on the surface or a sub-surface co-continuous with the external environment on a target cell. The target cell may be a cancer cell, a cell infected by a pathogen or parasite or other unwanted cell. A pathogen includes a eukaryotic or prokaryotic microorganism including a malaria parasite. It also includes a virus. Furthermore, a virally infected cell may express virally-derived receptors on its surface. Specific targeting of such a cell may result in loss of virus-producing cells. This would be an example of an unwanted cell.

The present invention is particularly useful in the generation of therapeutic agents to target cancer cells including leukocyte subsets. Cancer cells are generally defined by the expression of particular CD antigens. However, targeting a single CD antigen may cause collateral damage to normal cells which carry the same CD antigen. This problem is proposed to be solved by the present invention in that a single type of demibody alone would be incapable of inducing ADCC or CDC due to lack of a functional Fc domain and an inability to cross link. However, when two demibodies having complementary binding members are used which are directed to two different CD antigens or other antigens present on a cancer cell, then only cells with this unusual pair of surface molecules are cytotoxically targeted after both demibodies have bound. Once bound, the CD, antigen will move freely in the two dimensions of the lipid bilayer and the demibodies will eventually be in close proximity to each other. At that point, the members of the binding pair interact resulting in a binding pair and the two incomplete Fc domains form a functional Fc domain. Selective cytotoxicity is now induced for that cell. The essence of this aspect of the present invention is the unusual combination of surface molecules which correspond to particular cancer or unwanted cells or other target cells.

With respect to cancer treatment, CD antigens are particularly preferred such as two or more CD antigens selected from those listed in Table 2.

TABLE 2

Summary of CD antigens

| CD designation | Blood-related cancer |
| --- | --- |
| CD5 + CD19/CD20 | chronic lymphocytic leukemia (CLL) |
| CD19/CD20 + κ (or λ) | would target most clonal B-cell populations |
| CD19/CD20 + CD10 | follicular non-Hodgkins lymphoma (NHL) |
| CD19/CD20 + bcl-2 | follicular lymphoma (FL) CLL |
| CD103 + CD22 (or CD25) (or CD19) | hairy cell leukemia (HCL) |

TABLE 2-continued

Summary of CD antigens

| CD designation | Blood-related cancer |
| --- | --- |
| CD4 + CD8 | T-cell acute lymphocytic leukemia (T-ALL) ("cortical thymocyte") |
| CD8 + CD57 | NK cell/large granular lymphocyte leukemia |
| CD10 + CD34 | pre-B ALL |
| CD34 + myeloid marker (i.e. CD13 or CD33) | acute myeloid leukemia (AML) |
| CD117 (c-kit) + myeloid marker | AML |
| CD13 or CD33 (My) + CD14 (Mo) | myelomonocytic leukemias |
| CD41 or CD61 + CD33 | megakaryocytic leukemias |

The binding partners may constitute any of a number of entities which are capable of interacting with each other to form an association or bond. Examples of binding partners include complementary portions of a leucine zipper, a receptor-ligand (e.g. cytokine and cytokine receptor), actin and an actin-binding protein, DNA aptamers. The actual nature of the binding pairs is not critical to the present invention provided that upon coming together in two dimensions in close proximity, both members of the binding pair form an association or bond.

In a preferred embodiment, the binding pairs comprise complementary portions of a leucine zipper. Leucine zipper amino acid sequences are shown in Table 3. Heterodimerization occurs between for example SEQ ID NOs:1 and 2, SEQ ID NOs:3 and 4 and SEQ ID NOs:3 and 5. The length of the leucine zipper or other complementary binding portions include but is not limited to from 10 amino acids to 100 amino acid such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 amino acids.

TABLE 3

Leucine zipper sequences

| SEQUENCE ID NO: | SEQUENCE |
| --- | --- |
| 1 | LEI EAAFLEQ ENTALET EVAELEQ EVQRLEN EVSQYET RYGPLGGGK |
| 2 | KGGGLEI RAAFLRR RNTALRT RVAELRQ RVQRARN RVSQYRT RYGPL |
| 3 | LEI RAAFLRQ RNTALRT EVAELEQ EVQRLEN EVSQYET RYGPLGGGK |
| 4 | KGGGLEI EAAFLER ENTALET RVAELRQ RVQRARN RVSQYRT RYGPL |
| 5 | LEI EAAFLER ENTALET RVAELRQ RVQRLRN RVSQYRT RYGPLGGGK |
| 6 | GGTACCGATGATGATGATAAACAGGTGCAGCTGGTTGAAAGCGGCGGTGGTCTGGTTCAG CCGGGTGGCTCTCTGAAACTGAGCTGCGCGGCGTCTGGCTTTGATTTTAGTCGTTATTGG ATGAGCTGGGTTCGTCAGGCACCGGGTAAAGGCCTGGAATGGATTGGCGAAATTAATCCG ACGAGTAGCACCATTAATTTTACCCCGAGCCTGAAAGATAAAGTGTTCATTAGCCGTGAT AACGCGAAAAACACCCTGTACCTGCAGATGAGTAAAGTTCGCAGCGAAGATACCGCCCTG TATTATTGCGCACGTGGTAACTATTACCGTTACGGCGATGCCATGGATTATTGGGGTCAG GGCACCAGTGTTACCGTTAGCAAAATTAGCGGCGGCGGTGGTAGCGGTGGCGGTGGCAGC GGCGGTGGCGGCAGCGGTGGTGGCGGTAGCGGCGGCGGTGGTTCTAGTGATATCGTGCTG ACCCAGAGTCCGGCGAGCCTGGCCGTTTCTCTGGGTCAGCGTGCAACCATCAGCTGCCGC GCGAGCAAAAGTGTGAGCACCTCTGGTTATTCTTATCTGCATTGGTATCAGCAGAAACCG GGCCAGCCGCCGAAACTGCTGATTTATCTGGCGTCTAATCTGGAATCTGGCGTGCCGGCG CGCTTCAGCGGTTCTGGCAGTGGCACCGATTTTACCCTGAACATTCATCCGGTGGAAGAA GAAGATGCCGCCACCTATTACTGCCAGCATAGCCGTGAACTGCCGTTTACCTTTGGCAGC GGTACGAAACTGGAAATCAAAGTCGACGTGGTGGTGGTTCTGGTGGTGGTGGTAGCGGT GGCGGTGGTAGCGGTGGTGGCAGATCTATGGTCAGCAAAGGCGAAGAAAACAACATGGCA |

TABLE 3-continued

Leucine zipper sequences

| SEQUENCE ID NO: | SEQUENCE |
|---|---|
| | ATCATCAAAGAATTTATGCGTTTTAAAGTTCGCATGGAAGGCAGCGTTAACGGCCATGAG<br>TTTGAAATCGAAGGCGAAGGTGAAGGCCGTCCTTATGAAGGCTTCCAGACTGCTAAACTG<br>AAAGTCACAAAAGGCGGTCCGCTGCCTTTTGCATGGGATATTCTGACCCCTCAATTTACA<br>TACGGCAGCAAAGCGTATGTTAAACATCCGGCTGATATCCCTGATTATTTTAAGCTGTCT<br>TTTCCGGAAGGCTTTAAGTGGGAACGTGTGATGAACTTCGAAGATGGGGGGGTTGTGACC<br>GTGACCCAGGATTCATCTCTGCAGGATGGAGAATTTATTTATAAGGTAAAACTGCGTGGC<br>ACGAATTTCCCTAGCGATGGCCCAGTGATGCAGAAAAAGACCATGGGTTGGGAAGCTAGC<br>TCTGAACGTATGTATCCGGAGGATGGCGCTCTGAAAGGCGAGATCAAAATGCGTCTGAAA<br>CTGAAAGATGGTGGCCACTATACGTCCGAAGTAAAAACGACCTACAAAGCAAAAAAGCCG<br>GTTCAGCTGCCGGGTGCGTATATTGTCGGGATTAAACTGGATATTACAAGCCATAATGAA<br>GATTATACGATTGTGGAGCAATATGAACGTGCGGAAGGCCGCCACAGTACGGGTGGTATG<br>GATGAACTGTACAAACTCGAGGGTGGTGGTGGTAGCGGTGCTGGTGGTTCTGGTGCTGGC<br>GGTAGCGGTGGCGGTACTAGTGAAATTAGCGCCCTGGAAAAAGAAATCAGCGCGCTGGAA<br>AAAGAAATTAGCGCGCTGGAAAAAGCGAGCTAATAAGAATTC |
| 7 | GGTACCGACGACGACGACAAGATGGATGTGGTGATGACCCAGACCCCGGCGAGCCTGAGC<br>GCGAGCGTGGGCGAAACCGTCACCATTACCTGCCGTGCGAGCGGCAGCATTCATAACTAT<br>CTGGCGTGGTATCAGCAGAAACTGGGTAAAGCCCGCAGCTGCTGGTGTATAACGCGAAA<br>ACCCTGGCGGATGGTGTGCCGAGCCGTTTTAGCGGCAGCGGCAGCGGCACCCAGTTTAGC<br>CTGAAAATTAACAGCCTGCAGCCGGAAGATTTTGGCAGCTATTATTGCCAGCATTTTTGG<br>AGCATTCCGTGGACCTTTGGTGGTGGCACCAAACTGGAACTGAAACGTGGTGGCGGTGGT<br>GGCGGCGGTGGTAGCGGTGGCGGCGGCAGCGGTGGCGGTGGCAGCCAGGTGCAGCTGCAG<br>CAGAGCGGCACCGAACTGGTGAAACCGGTGGCGAGCGTGAAAATGAGCTGCAAAGCGAGC<br>GGCTTTACCTTTACCGATTATAATATGCATTGGGTGAAACAGACCCCGGGTCAGGGCCTG<br>GAATGGATTGGCGCGATTTATCCGGAAAACGGCGATACCAGCTATAACCAGCGCTTTAAA<br>GGCAAAGCGACCCTGACCGCGGATAAAAGCTTTAGCACCGCGTATATGCATCTGAGCAGC<br>CTGACCAGCGAAGATACCGCGGTGTATTTTGCGCGCGTTTTTATTATTATGGCAGCTAT<br>TATGGCGCGCTGGATTATTGGGGCCAGGGCACCAGCGTGACCGTGAGCAGCGATAGCGGC<br>GCGGAATTTGAAGTCGACGGTGGTGGCGGTTCTGGTGGTGGTGGTAGCGGTGGTGGTGGT<br>AGCGGCGGTGGTAGATCTATGAGCAAAGGCGAAGAACTGTTTACCGGCGTTGTTCCGATC<br>CTGGTGGAACTGGATGGCGATGTGAATGGCCATAAATTTAGCGTTAGCGGCGAAGGCGAA<br>GGCGATGCCACCTATGGCAAACTGACCCTGAAATTCATTTGCACCACCGGTAAACTGCCG<br>GTGCCGTGGCCGACCCTGGTGACCACCTTTAGCTATGGTGTGATGGTGTTTAGCCGTTAT<br>CCGGATCATATGAAACAGCATGATTTCTTTAAAAGCGCGATGCCGGAAGGCTATGTGCAG<br>GAACGTACCATTTTCTTTAAAGATGATGGCAATTATAAAACCCGTGCGGAAGTGAAATTT<br>GAAGGTGATACCCTGGTGAACCGCATTGAACTGAAAGGCATTGATTTTAAAGAAGATGGT<br>AATATCCTGGGCCACAAACTGGAATATAATTATAATAGCCATAATGTGTATATTATGGCG<br>GATAAACAGAAAAATGGCATCAAAGCGAACTTCAAAATTCGCCATAATATTGAAGATGGT<br>GGTGTGCAGCTGGCGGATCATTATCAGCAGAATACCCCGATTGGCGATGGCCCGGTTCTG<br>CTGCCGGATAACCATTATCTGAGCATTCAGAGCGCGCTGAGCAAAGATCCGAATGAAAAA<br>CGTGATCACATGGTTCTGCTGGAATTTGTGACCGCGGCGGGTATCACCCATGGTATGGAT<br>GAACTGTATAAACTCGAGGGTGGTGGTGGTTCTGGTGGTGGTGGTAGCGGCGGCGGTGGT<br>AGCGGTGGTGGTACTAGTAAAATTAGCGCGCTGAAAGAAAAAATTAGCGCCCTGAAAGAA<br>AAAATCAGCGCGCTGAAAGAAGCGAGCTAATAAGAATTC |
| 8 | GGGGS GGGGS GGGGS GGG |
| 9 | MSDKIIHLTDDSFDTDVLKADGAILVDFWAEWCGPCKMIAPILDEIADEY<br>QGKLTVAKLNIDQNPGTAPKYGIRGIPTLLLFKNGEVAATKVGALSKGQL<br>KEFLDANLAGSGSGHMHHHHHSSGLVPRGSGMKETAAAKFERQHMDSPD<br>LGTDDDDK<u>QVQLVESGGGLVQPGGSLKLSCAASGFDFSRYWMSWVRQAPG<br>KGLEWIGEINPTSSTINFTPSLKDKVFISRDNAKNTLYLQMSKVRSEDTA<br>LYYCARGNYYRYGDAMDYWGQGTSVTVSKISGGGGSGGGGSGGGGSGGGG<br>SGGGGSSDIVLTQSPASLAVSLGQRATISCRASKSVSTSGYSYLHWYQQK<br>PGQPPKLLIYLASNLESGVPARFSGSGSGTDFTLNIHPVEEEDAATYYCQ<br>HSRELPFTFGSGTKLEIK</u>vdGGGGSGGGGSGGGGSGGGrsMVSKGEENNM<br>AIIKEFMRFKVRMEGSVNGHEFEIEGEGEGRPYEGFQTAKLKVTKGGPLP<br>FAWDILSPQFTYGSKAYVKHPADIPDYFKLSFPEGFKWERVMNFEDGGVV<br>TVTQDSSLQDGEFIYKVKLRGTNFPSDGPVMQKKTMGWEASSERMYPEDG<br>ALKGEIKMRLKLKDGGHYTSEVKTTYKAKKPVQLPGAYIVGIKLDITSHN<br>EDYTIVEQYERAEGRHSTGGMDELYKleGGGGSGGGGSGGGGSGGGTSEI<br>SALEKEISALEKEISALEKAS |
| 10 | MSDKIIHLTDDSFDTDVLKADGAILVDFWAEWCGPCKMIAPILDEIADEY<br>QGKLTVAKLNIDQNPGTAPKYGIRGIPTLLLFKNGEVAATKVGALSKGQL<br>KEFLDANLAGSGSGHMHHHHHSSGLVPRGSGMKETAAAKFERQHMDSPD<br>LGTDDDDK<u>MDVVMTQTPASLSASVGETVTITCRASGSIHNYLAWYQQKLG<br>KSPQLLVYNAKTLADGVPSRFSGSGSGTQFSLKINSLQPEDFGSYYCQHF<br>WSIPWTFGGGTKLELKRGGGGGGGSGGGGSGGGGSQVQLQQSGTELVKP<br>VASVKMSCKASGFTFTDYNMHWVKQTPGQGLEWIGAIYPENGDTSYNQRF<br>KGKATLTADKSFSTAYMHLSSLTSEDTAVYFCARFYYYGSYYGALDYWGQ<br>GTSVTVSSDSGAEFE</u>vdGGGGSGGGGSGGGGSGGGrsMSKGEELFTGVVP<br>ILVELDGDVNGHKFSVSGEGEGDATYGKLTLKFICTTGKLPVPWPTLVTT<br>FSYGVMVFSRYPDHMKQHDFFKSAMPEGYVQERTIFFKDDGNYKTRAEVK<br>FEGDTLVNRIELKGIDFKEDGNILGHKLEYNYNSHNVYIMADKQKNGIKA |

TABLE 3-continued

Leucine zipper sequences

SEQUENCE
ID NO:   SEQUENCE

NFKIRHNIEDGGVQLADHYQQNTPIGDGPVLLPDNHYLSTQSALSKDPNE
         KRDHMVLLEFVTAAGITHGMDELyKleGGGGSGGGGSGGGGSGGGtsKIS
         ALKEKISALKEKISALKEAS

In one embodiment, the present invention contemplates a demibody comprising an Fab portion (scFv) or derivative thereof, an incomplete, non-functional Fc domain (Cγ2a or Cγ2b) which are members of a binding pair, and one member of a complementary binding pair wherein said demibody is capable of forming a functional Fc domain when the immunointeractive molecule is bound to a second complementary demibody comprising an Fab portion, an amount of an Fc domain required to complement the incomplete Fc domain on the first demibody to thereby form an active Fc domain with the other member of the binding pair.

Preferably, the binding pairs comprise a leucine zipper.

Preferably, the Fab portion is an scFv fragment.

Preferably, the Fab or scFv fragment has specificity for an antigen on a cancer cell such as a CD antigen.

The present invention provides, therefore, a set of demibodies wherein each set comprises at least two demibodies each having the structure:

x-(Fc$^I$)i-scFv(Ag$^1$); or y-(Fc$^{II}$)i-scFv(Ag$^2$);

wherein:
x and y are binding partners capable of forming an association or bond together;
(Fc$^I$)i and (Fc$^{II}$)i are each incomplete, non-functional Fc domains capable of forming a functional Fc domain upon binding of x and y; and
scFv(Ag$^1$) and scFv(Ag$^2$) are single chain variable fragments having specificity for two different antigens (Ag), Ag$^1$ or Ag$^2$.

Preferably, (Fc$^I$)i is the γ2a chain of the Fc domain and the (Fc$^{II}$)i is the γ2b chain of the Fc domain.

The present invention further contemplates a composition of matter comprising the demibodies:

x-(Fc$^I$)i-scFv(Ag$^1$); and y-(Fc$^{II}$)i-scFv(Ag$^2$).

As indicated above, the Fc portions may be replaced with an agent such as a dye or portions of an agent such as a cytotoxic molecule, therapeutic molecule or reporter molecule.

Hence, another aspect of the present invention provides, a set of demibodies wherein each set comprises at least two demibodies each having the structure:

x-(Mo$^I$)i-scFv(Ag$^1$); or y-(Mo$^{II}$)i-scFv(Ag$^2$);

wherein:
x and y are binding partners capable of forming an association or bond together;
(Mo$^I$)i and (Mo$^{II}$)i are each portions of a reporter molecule, cytotoxic molecule or therapeutic molecule or other agent capable of forming a functional reporter, cytotoxic or therapeutic molecule upon binding of x and y; and
scFv(Ag$^1$) and scFv(Ag$^2$) are single chain variable fragments having specificity for two different antigens (Ag), Ag$^1$ or Ag$^2$.

In relation to the above formulae the scFv may be replaced by another antigen binding portion of an immunoglobulin or any affinity scaffold such as but not limited to dAbs, nanobodies, microproteins, fibronectins, microbodies, anticalins, aptamers, darpins, avimers, afflins, and Kunitz domains.

The demibodies may be in different compositions or in the same composition. As stated above, multi-part pharmaceutical packs are contemplated in which the demibodies are admixed prior to use.

The demibodies of the present invention may need to be deimmunized prior to administration. The term "deimmunized" includes, in relation to humans, humanization. Any technique of deimmunization may be used including generating chimeric antibodies or grafting CDAs to an antibody.

The composition of this aspect of the present invention may also include one or more pharmaceutical carriers and/or diluents. The preparation of pharmaceutical compositions is well described in the art such as Remington's Pharmaceutical Sciences, 18$^{th}$ Ed. (Mack Publishing Company, Easton, Pa., U.S.A., 1990). As stated above, a particularly useful embodiment is directed to demibodies specific for CD antigens on cancer cells. Conveniently, the repertoires of the CD antigens expressed by cancer cells is determined by a CD antibody microarray.

A particularly useful microarray is disclosed in International Patent Application No. PCT/AU99/01156 (WO 00/39580).

Once the pattern of CD antigen expression is determined, demibodies specific for two CD antigens which are expressed on the target cells for example cancer cells but not commonly on normal cells are selected and used in therapy, for example cancer therapy.

A similar approach may also be adopted in order to target other cells such as virally infected cells.

In an alternative embodiment, the Fc portion comprises parts of a reporter molecule. When two demibodies are in close proximity, a functional reporter molecule capable of giving an identifiable signal is re-constituted. This enables the design of highly specific diagnostic and imaging agents.

Still yet another embodiment provides a portion of a drug or other therapeutic agent which reconstitutes when a pair of demibodies come together. The drug or therapeutic agent may also be internalized.

The present invention further contemplates a method for a method for diagnosing cancer in a subject said method comprising contacting putative cancer cells with a pair of demibodies wherein each demibody comprises first, second and third portions wherein said first portions are capable of interacting with one or two cancer specific antigens on the cell, said second portions comprise distinct reporter molecules or complementary non-functional portions of a single reporter molecule and said third portions are complementary binding pairs wherein upon binding of the individual demibodies to the two antigens, the binding pairs combine enabling the reporter molecules to provide a combined signal or to reconstitute a single reporter molecule. The first portion may be an antigen binding portion of an immunoglobulin or other affinity scaffold such as but not limited to dAbs, nanobodies, microproteins, fibronectins, microbodies, anticalins, aptamers, darpins, avimers, afflins, and Kunitz domains.

The present invention further provides a method for detecting a target molecule said method comprising contacting a sample putatively comprising said target molecule with a pair of demibodies wherein each demibody comprises first, second and third portions wherein said first portions are capable of interacting with a target molecule specific epitope, said second portions comprise distinct reporter molecules or complementary non-functional portions of a single reporter molecule and said third portions are complementary binding pairs wherein upon binding of the individual demibodies to the two epitopes, the binding pairs combine enabling the reporter molecules to provide a combined signal or to reconstitute a single reporter molecule. Preferably the target molecule is a cell product such as a protein including a post-translationally modified protein. Examples include a phosphorylated or glycosylated protein. Such proteins or their level of post-translational modification may be indicative of a disease condition or level of health.

The present invention is further described by the following non-limiting Examples.

In the Examples, the following materials and methods were employed:

Materials

RPMI 1640 medium (Hepes modification) was purchased from Sigma Aldrich (Castle Hill, NSW, Australia). Gentamicin (50 mg gentamicin sulfate/ml), L-glutamine (200 mM) and fetal calf serum (FCS) were from Invitrogen (Mulgrave, Victoria, Australia).

Demibody Design

The protein sequences (FIGS. 1A and B) were derived from:
- the fluorescence proteins (FPs) dsRED variant mOrange (Shaner et al, *Nature Biotechnology* 22:1567-1572, 2004) and GFP variant T-Sapphire (Zappater-Hommer and Griesbeck, *BMC Biotechnol* 3:5, 2003);
- a scFV CD45 (Lin et al, *Cancer Res* 66:3884-92, 2006);
- a scFV CD20 (Shan et al, *J. Immunol* 162:6589-95, 1999); and
- artificial leucine zippers (LZs) ISAL E3 and ISAL K3 (Litowski and Hodges, *J. Biol. Chem.* 277:37272-37279, 2002).

The Demibodies were designed as scFV-linker-FP-linker-LZ, in the following arrangements:
- Demibody A (DBA; CD45-mOrange-E3); and
- Demibody B (DBB; CD20-Sapphire-K3).

The linkers were (GGGGS GGGGS GGGGS GGG glycine serine) [SEQ ID NO:8]. A unique 6 bp restriction endonuclease site placed on each side of each linker at the gene level gave rise to pairs of additional residues.

Demibody Gene Synthesis, Protein Expression and Purification

The gene sequences were designed based on these protein sequences using *E. coli* codon preferences.

Protein Concentrations

Protein concentrations were estimated at $A_{280\ nm}$ using theoretical extinction coefficients of Abs 0.1% of 1.26 and 1.21 for Trx-DBA and Trx-DBB, respectively.

SEC/MALLS

The aggregation states of the proteins were assessed by SEC/MALLS (Size exclusion chromatography monitored by multi angle laser light scattering). Samples were filtered using a 0.22 µM filter and subjected to SEC on an Akta Basic (GE Healthcare) using a Superose-6 column (GE Healthcare) using a flow rate of 0.4 mL·min$^{-1}$. In addition to monitoring absorbance at (215 nm, 280 nm and 400 or 550 nm), the refractive index of the sample and scattering data at three different angles were monitored by in-line Optilab DSP Interferometric Refractometer and MiniDawn (Wyatt) instruments. BSA was used as a calibration standard.

Fluorescence Analysis

Fluorescence experiments were measured on a Cary Eclipse Fluorescence Spectrophotometer (Varian Inc., Palo Alto, Calif.). Proteins (0.1-0.9 mg/mL) in Tris-HCl (100 mM) NaCl (50 mM), pH 8.5 containing 5% v/v glycerol (0.1% v/v). 5-mm were used holding a volume of ~250 µL. T-Sapphire fluorescence and FRET were measured by excitation at 400 nm, and the fluorescence emission spectra recorded from 450-600 nm, using slit widths of 10 nm. mOrange fluorescence was measured by excitation at 510 nm and the fluorescence emission spectra recorded from 550-650 nm, using slit widths of 10 nm. Scans were recorded at a rate of 60 nm·min$^{-1}$. Data were processed using Scan Software v.1.1.

Cell Lines and their Culture

MEC1 cells were obtained from the Dipartimento di Scienze Biomediche e Oncologia Umana, Universita di Torino, Ospedale Mauriziano Umberto 1°, Italy. Raji cells (B-cell Burkitt's lymphoma) and CCRF-CEM cells (T-cell acute lymphocytic leukaemia) were from the American Type Culture Collection (Manassas, Va., USA). Cell lines were grown in RPMI 1640 medium supplemented with 10% v/v FCS, 50 µg/mL gentamicin and 2 mM L-glutamine at 37° C. in a non-humidified atmosphere. Samples of cell cultures (10 mL) were harvested at a density of $8 \times 10^5$ cells/mL by centrifugation (600 g, 10 min, 4° C.), washed in an equal volume of Hanks solution and resuspended in Hanks solution for interaction with one or both Demibodies.

Flow Cytometry

Cells ($2 \times 10^6$) were washed twice in PBS and resuspended in 2.0 mL of FACS buffer (PBS with 5% v/v fetal calf serum, FCS). Aliquots (300 µL, $3 \times 10^5$ cells) were mixed with the Demibody (~200 µg/mL, 20 µL) and incubated at room temperature, in the dark, for one hour. Samples were analysed on a LSR II flow cytometer (Becton Dickinson, Franklin Lakes, N.J., USA). Data were collected and analyzed using LSR software (Becton Dickenson). Data from a minimum of 10,000 events were collected.

Example 1

Generation of Demibodies

Figure 2C:
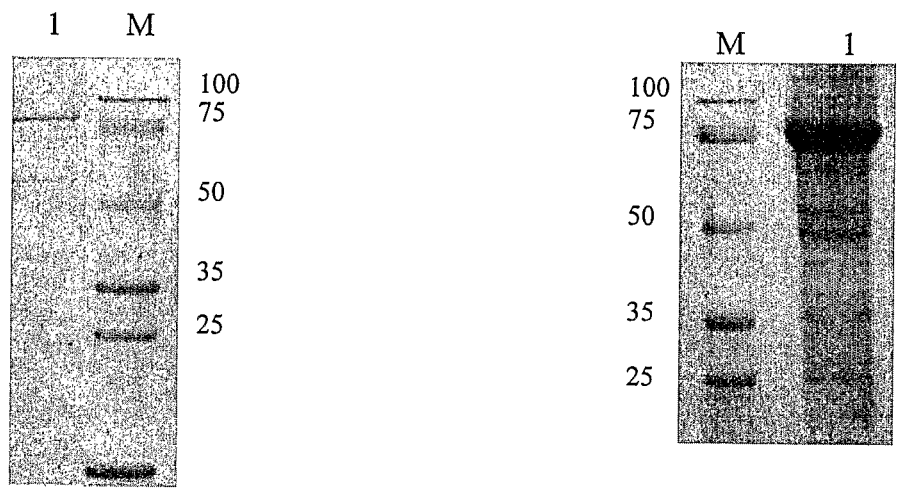

The genes encoding DBA and DBB were synthesized (Schemes 1 and 2) and cloned into the pET32a vector to generate pET32a-30103s1, and pET32a-30103s2. After transformation into *E. coli* BL-21(DE3), several colonies from each transformation were selected, and tested for protein expression. The appearance of a band at ~78 kDa from an induced sample was taken to represent the successful expression of the proteins and highly expressing colonies (colony 5 for pET32a-30103s1pET32a 30103s2, and colony 3 for pET32a-30103s2) were used in successive expression experiments (FIGS. 2A, B). In both cases the proteins were expressed as inclusion bodies so after large-scale expression (1L), the proteins were purified by metal affinity chromatography under denaturing conditions, and refolded to yield a final protein concentration of 0.1 and 0.9 mg/mL for Trx-DBA and Trx-DBB, respectively. The refolded proteins were ~80% pure as judged by SDS-PAGE (FIG. 2C).

Scheme 1: DNA sequence of synthetic 30103 S1 (SEQ ID NO: 6)
GGTACCGATGATGATGATAAACAGGTGCAGCTGGTTGAAAGCGGCGGTGGTCTGGTTCAG

CCGGGTGGCTCTCTGAAACTGAGCTGCGCGGCGTCTGGCTTTGATTTTAGTCGTTATTGG

ATGAGCTGGGTTCGTCAGGCACCGGGTAAAGGCCTGGAATGGATTGGCGAAATTAATCCG

ACGAGTAGCACCATTAATTTTACCCCGAGCCTGAAAGATAAAGTGTTCATTAGCCGTGAT

AACGCGAAAAACACCCTGTACCTGCAGATGAGTAAAGTTCGCAGCGAAGATACCGCCCTG

TATTATTGCGCACGTGGTAACTATTACCGTTACGGCGATGCCATGGATTATTGGGGTCAG

GGCACCAGTGTTACCGTTAGCAAAATTAGCGGCGGCGGTGGTAGCGGTGGCGGTGGCAGC

GGCGGTGGCGGCAGCGGTGGTGGCGGTAGCGGCGGCGGTGGTTCTAGTGATATCGTGCTG

ACCCAGAGTCCGGCGAGCCTGGCCGTTTCTCTGGGTCAGCGTGCAACCATCAGCTGCCGC

GCGAGCAAAAGTGTGAGCACCTCTGGTTATTCTTATCTGCATTGGTATCAGCAGAAACCG

GGCCAGCCGCCGAAACTGCTGATTTATCTGGCGTCTAATCTGGAATCTGGCGTGCCGGCG

CGCTTCAGCGGTTCTGGCAGTGGCACCGATTTTACCCTGAACATTCATCCGGTGGAAGAA

GAAGATGCCGCCACCTATTACTGCCAGCATAGCCGTGAACTGCCGTTTACCTTTGGCAGC

GGTACGAAACTGGAAATCAAAGTCGACGGTGGTGGTGGTTCTGGTGGTGGTGGTAGCGGT

GGCGGTGGTAGCGGTGGTGGCAGATCTATGGTCAGCAAAGGCGAAGAAAACAACATGGCA

ATCATCAAAGAATTTATGCGTTTTAAAGTTCGCATGGAAGGCAGCGTTAACGGCCATGAG

TTTGAAATCGAAGGCGAAGGTGAAGGCCGTCCTTATGAAGGCTTCCAGACTGGTAAACTG

AAAGTCACAAAAGGCGGTCCGCTGCCTTTTGCATGGGATATTCTGAGCCCTCAATTTACA

TACGGCAGCAAAGCGTATGTTAAACATCCGGCTGATATCCCTGATTATTTTAAGCTGTCT

TTTCCGGAAGGCTTTAAGTGGGAACGTGTGATGAACTTCGAAGATGGGGGGGTTGTGACC

GTGACCCAGGATTCATCTCTGCAGGATGGAGAATTTATTTATAAGGTAAAACTGCGTGGC

ACGAATTTCCCTAGCGATGGCCCAGTGATGCAGAAAAAGACCATGGGTTGGGAAGCTAGC

TCTGAACGTATGTATCCGGAGGATGGCGCTCTGAAAGGCGAGATCAAAATGCGTCTGAAA

CTGAAAGATGGTGGCCACTATACGTCCGAAGTAAAAACGACCTACAAAGCAAAAAAGCCG

GTTCAGCTGCCGGGTGCGTATATTGTCGGGATTAAACTGGATATTACAAGCCATAATGAA

GATTATACGATTGTGGAGCAATATGAACGTGCGGAAGGCCGCCACAGTACGGGTGGTATG

GATGAACTGTACAAACTCGAGGGTGGTGGTGGTAGCGGTGGTGGTGGTTCTGGTGGTGGC

GGTAGCGGTGGCGGTACTAGTGAAATTAGCGCCCTGGAAAAAGAAATCAGCGCGCTGGAA

AAAGAAATTAGCGCGCTGGAAAAAGCGAGCTAATAAGAATTC

Scheme 2: DNA sequence of synthetic 30103 S2 (SEQ ID NO: 7)
GGTACCGACGACGACGACAAGATGGATGTGGTGATGACCCAGACCCCGGCGAGCCTGAGC

GCGAGCGTGGGCGAAACCGTGACCATTACCTGCCGTGCGAGCGGCAGCATTCATAACTAT

CTGGCGTGGTATCAGCAGAAACTGGGTAAAGCCCGCAGCTGCTGGTGTATAACGCGAAA

ACCCTGGCGGATGGTGTGCCGAGCCGTTTTAGCGGCAGCGGCAGCGGCACCCAGTTTAGC

CTGAAAATTAACAGCCTGCAGCCGGAAGATTTTGGCAGCTATTATTGCCAGCATTTTTGG

AGCATTCCGTGGACCTTTGGTGGTGGCACCAAACTGGAACTGAAACGTGGTGGCGGTGGT

GGCGGCGGTGGTAGCGGTGGCGGCGGCAGCGGTGGCGGTGGCAGCCAGGTGCAGCTGCAG

CAGAGCGGCACCGAACTGGTGAAACCGGTGGCGAGCGTGAAAATGAGCTGCAAAGCGAGC

GGCTTTACCTTTACCGATTATAATATGCATTGGGTGAAACAGACCCCGGGTCAGGGCCTG

GAATGGATTGGCGCGATTTATCCGGAAAACGGCGATACCAGCTATAACCAGCGCTTTAAA

GGCAAAGCGACCCTGACCGCGGATAAAAGCTTTAGCACCGCGTATATGCATCTGAGCAGC

-continued

```
CTGACCAGCGAAGATACCGCGGTGTATTTTTGCGCGCGTTTTTATTATTATGGCAGCTAT

TATGGCGCGCTGGATTATTGGGGCCAGGGCACCAGCGTGACCGTGAGCAGCGATAGCGGC

GCGGAATTTGAAGTCGACGGTGGTGGCGGTTCTGGTGGTGGTGGTAGCGGTGGTGGTGGT

AGCGGCGGTGGTAGATCTATGAGCAAAGGCGAAGAACTGTTTACCGGCGTTGTTCCGATC

CTGGTGGAACTGGATGGCGATGTGAATGGCCATAAATTTAGCGTTAGCGGCGAAGGCGAA

GGCGATGCCACCTATGGCAAACTGACCCTGAAATTCATTTGCACCACCGGTAAACTGCCG

GTGCCGTGGCCGACCCTGGTGACCACCTTTAGCTATGGTGTGATGGTGTTTAGCCGTTAT

CCGGATCATATGAAACAGCATGATTTCTTTAAAGCGCGATGCCGGAAGGCTATGTGCAG

GAACGTACCATTTTCTTTAAAGATGATGGCAATTATAAAACCCGTGCGGAAGTGAAATTT

GAAGGTGATACCCTGGTGAACCGCATTGAACTGAAAGGCATTGATTTTAAAGAAGATGGT

AATATCCTGGGCCACAAACTGGAATATAATTATAATAGCCATAATGTGTATATTATGGCG

GATAAACAGAAAAATGGCATCAAAGCGAACTTCAAAATTCGCCATAATATTGAAGATGGT

GGTGTGCAGCTGGCGGATCATTATCAGCAGAATACCCCGATTGGCGATGGCCCGGTTCTG

CTGCCGGATAACCATTATCTGAGCATTCAGAGCGCGCTGAGCAAAGATCCGAATGAAAAA

CGTGATCACATGGTTCTGCTGGAATTTGTGACCGCGGCGGGTATCACCCATGGTATGGAT

GAACTGTATAAACTCGAGGGTGGTGGTGGTTCTGGTGGTGGTGGTAGCGGCGGCGGTGGT

AGCGGTGGTGGTACTAGTAAAATTAGCGCGCTGAAAGAAAAAATTAGCGCCCTGAAAGAA

AAAATCAGCGCGCTGAAAGAAGCGAGCTAATAAGAATTC
```

Expression of Soluble Demibody Proteins from the Origami Strain of E. coli

Figure 2D:
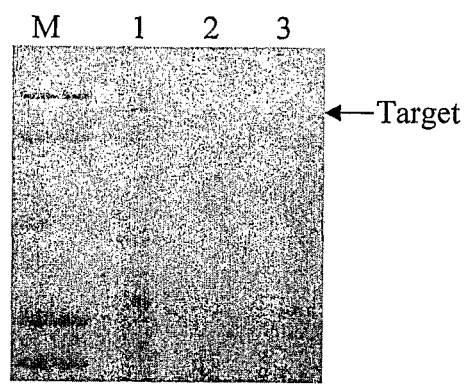

The gene DBB was subcloned into the pGS21a vector resulting in the vector pGS21a-30103s2, which encodes His$_6$-GST-DDB. This vector and the pGEX-30103s1 were transformed into the Origami (Novagen) E. coli strain, and highly expressing transformants were selected as described above for the BL21(DE3) strain. Both Trx-DBA and His$_6$-GST-DBB were expressed in the soluble fraction with 50% soluble protein (FIG. 2D).

Fluorescence Properties of Refolded Trx-Demibodies

Figure 3:
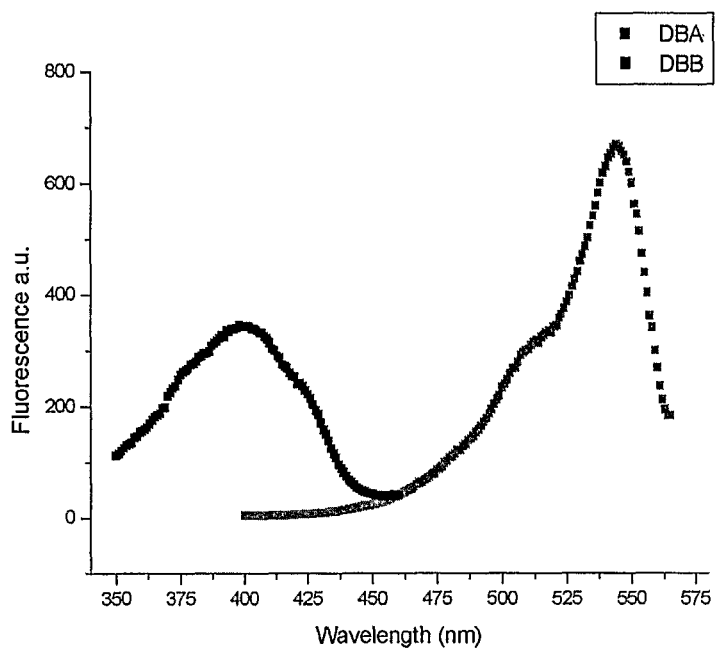
FIG. 3 is a graphical representation showing fluorescence excitation spectra of the refolded TRX Demibodies. The emission wavelength was set at 580 run for TRX-DBA and 510 run for TRX-DBB. The slit widths were both 10 nm and concentrations of the proteins were 0.1 mg/mL and ~0.9 mg/mL, respectively. Fluorescence excitation spectra were recorded from 400-560 nm for TRX-DBA and 350-460 nm for TRX-DBB.
Figure 4:
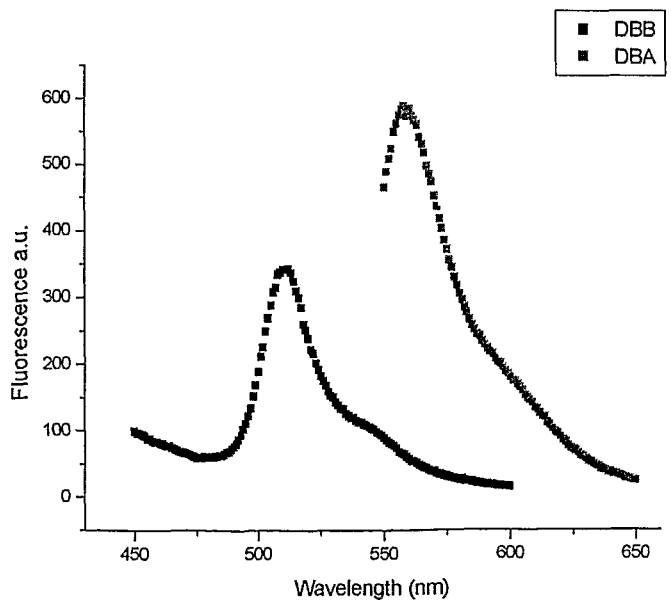
FIG. 4 is a graphical representation showing fluorescence emission spectra of the refolded TRX Demibodies. The excitation wavelength was set at 510 nm for TRX-DBA and 400 nm for TRX-DBB. The slit widths were both 10 nm and concentrations of the proteins were 0.1 mg/mL and -0.9 mg/mL, respectively. Fluorescence emission spectra were recorded from 550-650 nm for TRX-DBA and 450-600 nm for TRX-DBB 5.

Fluorescence excitation spectra were recorded for TRX-DBA and TRX-DBB. The emission wavelength was set at or as close to the theoretical maximum for each protein as was practical. TRX-DBA (orange) and TRX-DBB (blue) showed excitation maxima at ~344 nm and 400 nm as expected for their GFP-variant components, mOrange and T-Sapphire, respectively (FIG. 3). Fluorescence emission spectra were recorded for TRX-DBA and TRX-DBB. TRX-DBA (orange) and TRX-DBB (blue) showed emission maxima at ~510 nm and ~560 nm as expected for mOrange and T-Sapphire, respectively (FIG. 4).

Estimation of Active Concentrations of Refolded Trx-Demibodies

Figure 5:
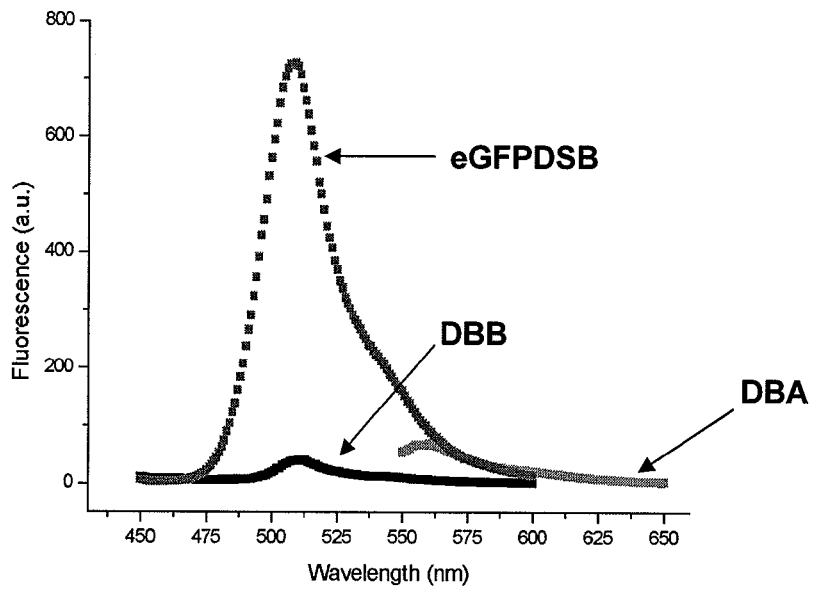
FIG. 5 is a graphical representation showing relative fluorescence properties of Demibodies. An eGFP fusion protein (1 μM) was excited at 430 nM; Refolded Trx-DBA (~1.5 μM) was excited at 510 nm; refolded Trx-DBB(~15 μM) was excited at 400 nm. Excitation and emission slit widths were both 5 nm in all cases.

Size exclusion chromatography, in combination with MALLS indicated that the refolded proteins contained a wide range of sized molecules, most likely arising from incorrectly folded protein. The fluorophores in GFP only form when the GFPs are correctly folded, and in general, GFPs are only fluorescent when the proteins they are fused to are also folded and soluble. Thus relative fluorescence was used to gauge the approximate concentration of active protein in each sample. The fluorescence properties of a 1-μM sample of a known eGFP-fusion protein were assessed. When an excitation wavelength of 430 nm (close to the fluorescence excitation maximum) was used the sample showed strong fluorescence emission at ~510 nm (FIG. 5). This was compared with the fluorescence properties of the TRX-DBA and TRX-DBB samples recorded under similar conditions (FIG. 4). The fluorescence maximum signal in each case was <10% of the eGFP. As the concentrations of those proteins were ~1.5 μM and ~15 μM, respectively, it was likely that the refolded preparations of Trx-DBA and Trx-DBB contained ≤~8% and ≤~0.5% properly refolded protein, respectively.

Ammonium Sulfate Fractionation

Because most of the DBA and DBB protein was incorrectly folded, the total sample (30 mL) of each Demibody was subjected to fractionation with 60% saturation ammonium sulfate. Solid AS was added stepwise to the dilute Demibody solution and dissolved by grinding with a glass rod. The solutions were then left for 30 min on ice. The precipitated protein was collected by centrifugation (10,000 g, 30 min, 4° C.), the inside of the tube was carefully dried with a tissue, and the protein was redissolved in 0.5 mL of PBS, again with grinding using a glass rod. Insoluble material, probably denatured inactive Demibody, was removed by centrifugation (10,000 g, 30 min, 4° C.). Residual ammonium sulfate in these concentrated Demibody solutions was removed by buffer exchange using Centricon centrifugal concentrators. Flow cytometric results obtained with these fractionated and concentrated Demibody solutions showed significant removal of inactive protein in this step.

Förster Resonance Energy Transfer

Figure 6:
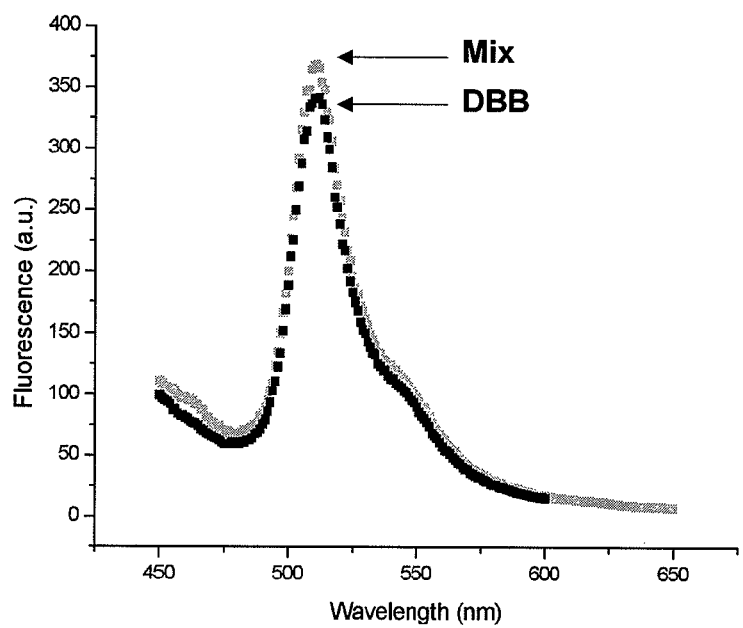
FIG. 6 is a graphical representation showing fluorescence properties of a mixture of TRX-DBA and TRX-DBB. The excitation wavelength was set at 400 nm for TRX-DBB; the slit widths were both 10 nm and concentrations of the proteins were 0.05 mg/mL and ~0.45 mg/mL, respectively for TRX-DBA and TRX-DBB. This corresponds to estimated active concentrations of ≤~130 nM and ≤~75 nM. A fluorescence emission spectrum was recorded from 450-600 nm for a mixture of TRX-DBA and TRX-DBB (ABMIX) and is compared with that of TRX-DBB alone.

In the absence of cells to which both DBA and DBB bind, and at protein concentrations below $10^{-5}$ $M^{-1}$, no FRET should be observed. The emission spectrum of a mixture of TRX-DBA and TRX-DBB was recorded (FIG. 6). It was essentially identical to that of TRX-DBB, showing no indication of FRET (as would be demonstrated by a decrease in the intensity of the emission peak at 510 nm and the appearance of an additional peak at ~560 nm).

Fluorescence Analysis of Cells Labeled with Demibodies by Flow Cytometry

Suspensions of the human cell lines Raji (CD20+, CD45+), MEC-2 (CD20+, CD45+), CCRF-CEM (CD20−, CD45+) were harvested (500 g, 10 min, room temperature), washed with PBS+5% v/v FCS, centrifuged and resuspended in PBS+5% v/v FCS to a final concentration of 1×10$^6$ cells/mL. To label cells with one or both Demibodies, 300 μL cell suspension (3×10$^5$ cells) was incubated with 30 μL Demibody (200 μg/mL, Demibody A (DBA; CD45-mOrange-E3), Demibody B (DBB; CD20-T-Sapphire-K3)) for 60 min in the dark at room temperature. Based upon the known immunophenotypes of these cell lines, the following binding patterns are expected.

| DBA | CD45-mOrange-E3 | bind to Raji, MEC-2, CCRF-CEM |
|---|---|---|
| DBB | CD20-T-Sapphire-K3 | bind to Raji, MEC-2 |

Following incubation, the labeled cells were analyzed by flow cytometry using a Becton Dickinson LSR II. The wavelength for detection of emission is listed followed by the band-width of the filter.

|  | DBA (mOrange) | DBB (T-Sapphire) | DBA + DBB FRET |
|---|---|---|---|
| Excitation | 488 nm | 407 nm | 407 nm |
| Emission | 575/26 nm | 525/50 nm | 585/42 nm |

The results obtained using flow cytometry are summarized in Table 4. The more than 7-fold shift in mean fluorescence detected at 575 nm (red numbers) indicates the binding of DBA to all three cell lines as expected, since they express CD45 which binds to DBA. A minor shift in fluorescence was detected for the binding of DBB on Raji and MEC-2 cells. A minor FRET signal was detected for the Raji cell line. These data are also presented in Table 5 as a ratio with fluorescence values for cells alone. The presence of binding and FRET for combinations of cells and Demibodies is summarised in Table 6.

The data (Tables 4-6) show that DBA (CD45-mOrange-E3) binds strongly to all 3 cell lines, since they all express the pan leukocyte marker, CD45. The data also show significantly greater binding of DBB (CD20-T-Sapphire-K3) to Raji and MEC-2 cells that express the B-lymphoid marker, CD20. Significant FRET was observed for Raji+DBA+DBB, but not for MEC-2. This discrepancy would be due to lower expression of CD20 on MEC-2, and the low proportion of active DBB in the current preparation. Excitation of (Raji cells+DBA+DBB) with light of 407 nm yielded FRET with emitted light at the long wavelength of 585 nm. This FRET can only be explained by combination of DBA and DBB at the surface of Raji cells via the complementary leucine zippers included in the constructs (FIGS. 1A and B). No such FRET was observed for DBA+DBB with cells omitted (FIG. 6).

TABLE 4

Flow cytometric analysis of cells labeled with Demibodies. The mean fluorescence is provided for combinations of cells and Demibodies at the indicated wavelengths. The fluorescence of T-Sapphire on DBB (CD20-T-Sapphire-K3) is highlighted in blue, fluorescence of mOrange on DBA (CD45-mOrange-E3) in orange, and the Forster resonance energy transfer (FRET) in red.

| | Excitation/emission | | |
|---|---|---|---|
| Cell line/Demibody | 407/525 nm binding of DBB | 488/575 nm binding of DBA | 407/585 nm FRET |
| Raji cells | 222 | 218 | 998 |
| Raji + DBA | 293 | 1678 | 1399 |
| Raji + DBB | 380 | 306 | 1408 |
| Raji + DBA + DBB | 387 | 1301 | 1551 |
| MEC-2 cells | 210 | 247 | 929 |
| MEC-2 + DBA | 242 | 1926 | 1139 |
| MEC-2 + DBB | 375 | 307 | 1231 |
| MEC-2 + DBA + DBB | 335 | 1416 | 1239 |
| CCRF-CEM cells | 280 | 323 | 1261 |
| CCRF-CEM + DBA | 289 | 2411 | 1414 |
| CCRF-CEM + DBB | 379 | 384 | 1360 |
| CCRF-CEM + DBA + DBB | 389 | 1623 | 1454 |

TABLE 5

Flow cytometric analysis of cells labeled with Demibodies Values for fluorescence are expressed as ratios of (cells + Demibody)/(cells) as indicated using the data from Table 4.

| Cell line | Binding of DBB Ratio of the mean fluorescence (cells + Demibody/cells) | Binding of DBA Ratio of the mean fluorescence (cells + Demibody/cells) | FRET Ratio of the mean fluorescence (cells + Demibody/cells) |
|---|---|---|---|
| Raji | 1.7 | 7.7 | 1.6 |
| MEC-2 | 1.8 | 7.8 | 1.3 |
| CCRF-CEM | 1.4 | 7.5 | 1.2 |

TABLE 6

Flow cytometric analysis of cells labeled with Demibodies The observation of binding of a Demibody to a particular cell line is indicated by +/− notation with FRET found only for Raji cells with DBA + DBB, using the data from Table 4. ++ strong binding of Demibody to cell, + binding of Demibody to cell, +/− weak binding of Demibody to cell (background).

| Cell line | Binding of DBB | Binding of DBA | DBA + DBB FRET |
|---|---|---|---|
| Raji | + | ++ | Yes |
| MEC-2 | + | ++ | No |
| CCRF-CEM | +/− | ++ | No |

Example 2

Expression and Purification

Subcloning 30103 S1 into pET32 Vector (1) The 30103 S1 gene was synthesized and cloned to pET32 vector using Kpn I and Hind III.

(2) The resulted clone pET-30103 S1 was verified by DNA sequencing.

Figure 7:
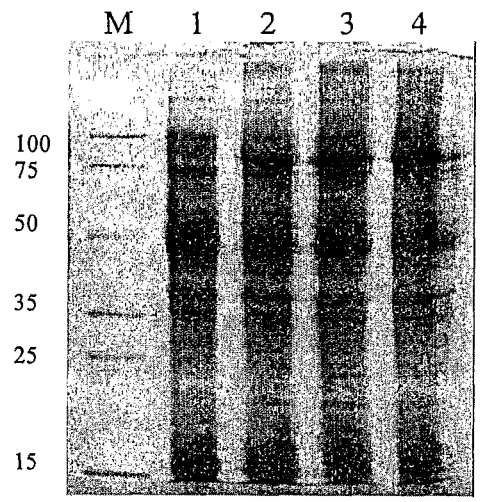
FIG. 7 is a photographic representation of the identification of pET32a-30103 S1 in E. coli BL21. M=Marker; 1=Uninduced colony; 2=Colony 1; 3=Colony 2; 4=Colony 3.
Figure 8:
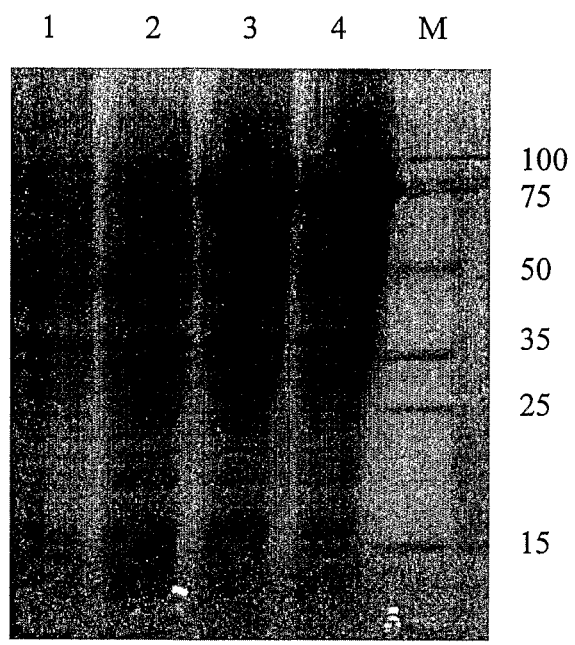
FIG. 8 is a photographic representation showing the solubility detection of 30103 S1. 1=supernatant of 30103 S1 induced at 15° C. overnight; 2=supernatant of 30103 S2 induced at 25° C. for 6 hours; 3=precipitation of 30103 S1 induced at 15° C. for overnight; 4=precipitation of 30103 S1 induced at 25° C. for 6 hours; M=low weight marker.
Figure 9:
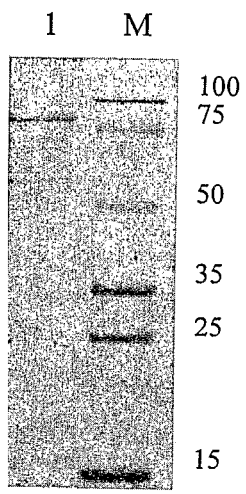
FIG. 9 is a diagrammatic representation showing SDS-PAGE of Refolded 30103 S1. M=marker; 1=refolded 30103 S1.

Transformation of *E. coli* BL-21(DE3)
  (3) Five nanogram of the pET-30103 S1 plasmid was transformed into *E. coli* BL-21(DE3).
  (4) Three colonies were selected. These clones were inoculated and grown in LB media and induced by 0.5 mM/L IPTG for 4 hr at 37° C. The expression results were detected by SDS-PAGE (12% w/v) (FIG. 7). Colony 3 was selected for future expression.
Optimization
  (5) The fusion protein was expressed at 25° C. and 15° C. The results are shown in FIG. 8.
Protein Expression
  (6) The *E. coli* strain was cultured in 1 L LB media for 4 hours and then induced by 0.5 mM/L IPTG for a further 4 hours at 37° C.
  (7) The cells were harvested by centrifugation. The cell paste was resuspended in 70 mL PBS and then sonicated on ice.
Protein Purification
  (8) The lysate after sonication was centrifuged at high speed for 10 min, and the inclusion bodies collected.
  (9) The inclusion bodies were washed twice with 2 M urea, 2% v/v Triton X-100, 5 mM EDTA, 0.5% BME, 1 M NaCl, 100 mM Tris-HCl buffer, pH 8.0 and water, respectively.
  (10) The inclusion bodies were resolved by 8 M urea, 20 mM Phosphate buffer, pH8.0 and then centrifuged to keep the supernatant.
  (11) The inclusion bodies were refolded by dialyzing against 100 mM Tris Cl, 50 mM NaCl and 5% v/v glycerol, pH 8.5 with a final concentration of 0.1 mg/mL. The refolded protein was detected by SDS-PAGE as shown in FIG. 9.

Example 3

Expression and Purification

Figure 10:
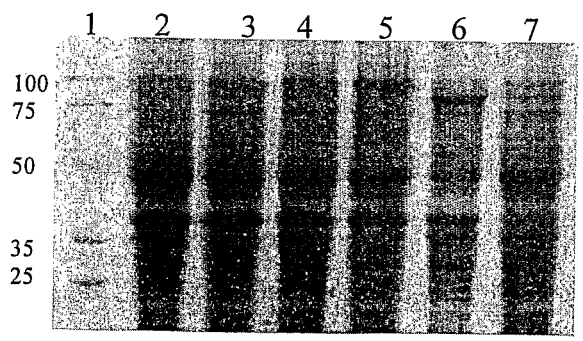
FIG. 10 is a photographic representation of the identification of the identification of pET32a-30103s2 in E. coli BL21. 1=marker; 2=colony #1 uninduced; 3-7=colony #2-#6 induced.
Figure 11:
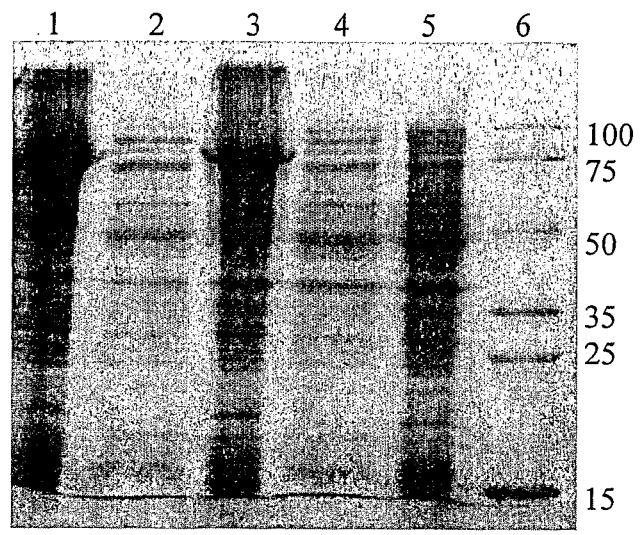
FIG. 11 is a photographic representation showing the solubility detection of 30103s2. 1=precipitate of 30103s2 induced at 15° C. overnight; 2=supernatant of 30103s2 induced at 15° C. overnight; 3=precipitate of 30103s2 induced at 25° C. for 6 hours; 4=supernatant of 30103s2 induced at 25° C. for 6 hours.
Figure 12:
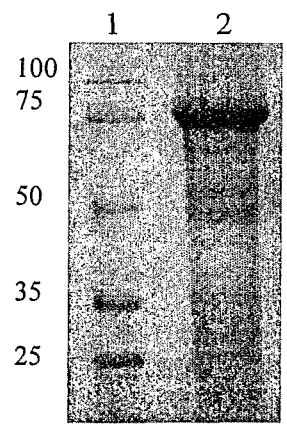
FIG. 12 is a photographic representation of the SDS-PAGE of Refolded 30103S2.1=marker; 2=refolded 30103 S2.

Subcloning 30103 S2 into pET32 Vector
  (1) The 30103 S1 gene was synthesized and cloned to pET32 vector using Kpn I and Hind III.
  (2) The resultant clone pET-30103 S2 was verified by DNA sequencing. Transformation of *E. coli* BL-21(DE3)
  (3) Five nanogram of the pET-30103 S2 plasmid was transformed into *E. coli* BL-21(DE3).
  (4) Seven colonies were selected. These clones were inoculated and grown in LB media and induced by 0.5 mM/L IPTG for 4 hr at 37° C. The expression_results were detected by SDS-PAGE (12% w/v) (FIG. 10). Colony 5 was selected for future expression.
Optimization
  (5) The fusion protein was expressed at 25° C. and 15° C. The results are shown in FIG. 11.
Protein Expression
  (6) The *E. coli* strain was cultured in 1 L LB media for 4 hours and then induced by 0.5 mM/L IPTG for a further 4 hours at 37° C.
  (7) The cells were harvested by centrifugation. The cell paste was resuspended in 70 mL PBS and then sonicated on ice.
Protein Purification
  (8) The lysate after sonication was centrifuged at high speed for 10 min, and the inclusion bodies were collected.
  (9) The inclusion bodies were washed twice with 2 M urea, 2% v/v Triton X-100, 5 mM EDTA, 0.5% BME, 1 M NaCl, 100 mM Tris-HCl buffer, pH 8.0 and water, respectively.
  (10) The inclusion bodies were resolved by 8 M urea, 20 mM Phosphate buffer, pH 8.0 and then centrifuged to keep the supernatant.
  (11) The inclusion bodies were refolded by dialyzing against 100 mM Tris Cl, 50 mM NaCl and 5% glycerol, pH 8.5 with a final concentration of 0.1 mg/mL. The refolded protein was detected by SDS-PAGE as shown in FIG. 12.

Example 4

Figure 13:
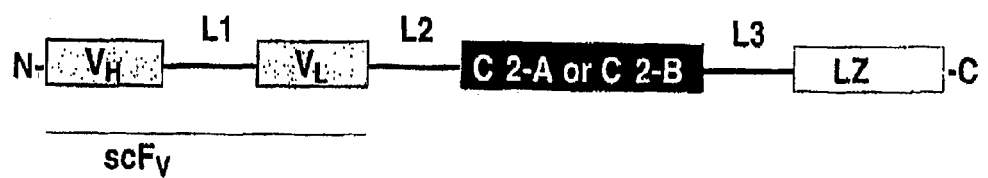
FIG. 13 is a schematic representation showing the polypeptide domains of proposed chimeric antibody (demibody).
Figure 14:
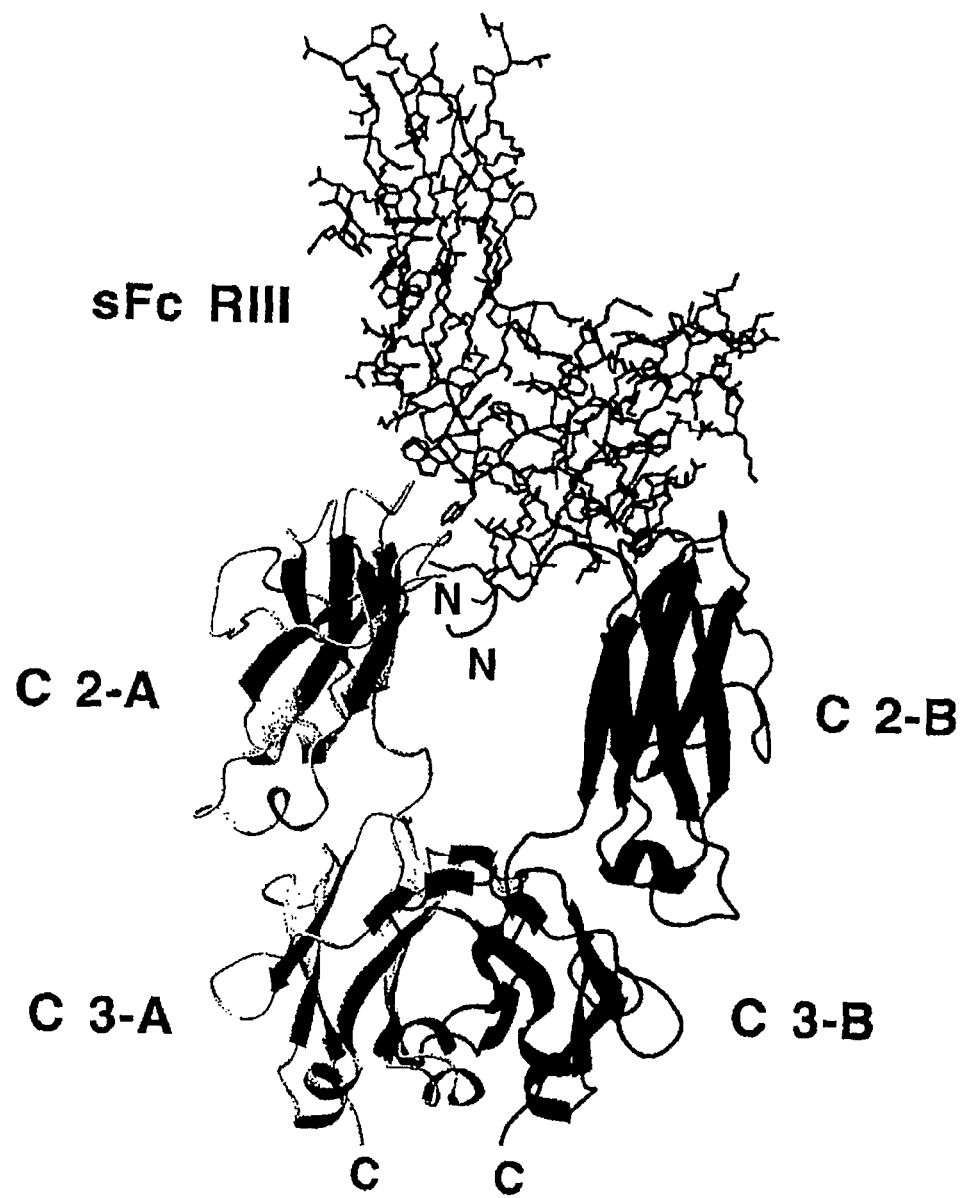
FIG. 14 is a diagrammatic representation showing the structure of protein components of the hIgG1 Fc fragment-Fc RIII complex. hIgG1 Fc fragment is shown as ribbon diagram with chain A (light) and chain B (dark). The N and C termini are indicated. sFc III is shown as a wire representation (coordinates taken from RCSB Protein Databank Accession code: 1e4k; Sondermann et al, Nature 406:267-273, 2000).

Construction of scFv Fragments scFv fragments are derived from whole antibodies. They are constructed by linking the antigen-binding $V_H$ and $V_L$ domains of an antibody with a flexible polypeptide linker. The linker may comprise a combination of glycine and serine residues to provide flexibility and to enhance hydrophilicity of the peptide backbone to allow hydrogen bonding with solvent molecules as well as being resistant to protease digestion. The construction of scFv fragments is described in Kort et al. (2001) supra and in publications described therein. A schematic representation showing polypeptide segments in the demibody is shown in FIG. 13. A diagram of the structural components of the human IgGI Fc fragment is shown in FIG. 14. The Fc domain is preferably divided into the γ2a and γ2b chains. This is useful in generating the Fc portion of the demibody. FIG. 15 shows heterodimerization of the leucine zipper.

Example 5

Generation of Antibodies

Antibodies specific for target antigens are used to develop scFv fragments. Antigens (e.g. CD antigens) from target cells in isolated form or in recombinant or synthetic form, or whole cells expressing surface antigens, are used to develop monoclonal or polyclonal antibodies. The antibodies are isolated and scFv fragments generated as described in Examples 1 and 2.

Example 6

Tools for Diagnostics and Research

Bispecific antibodies are used for diagnostics as reagents which bind to a specific marker and provide a binding site for an agent which would enable detection of the antibody. For example, in Positron-Emission-Tomography (PET) applications, the bispecific antibody provides a binding site for a radio-label.

Demibodies enable enhanced diagnostic applications such as fluorescence-activated cell sorting (FACS), fluorescence microscopy and immunoassays. The unifying principle is that a signal is only obtained after zipping of the two scFv-fusion proteins, either by indirect labeling of the newly formed Fc domain with a fluorescence or enzyme-labeled anti-Fc-antibody, or by so called "protein fragment complementation" (PCA), where each scFv-fusion protein would contain the half of an enzyme or fluorescent protein and only after zipping such an enzyme or fluorescent protein becomes active. In principle, this would be a combination of the demibody and PCA/bi-molecular fluorescent complementation (BiFC) approaches.

FACS

Figure 16:
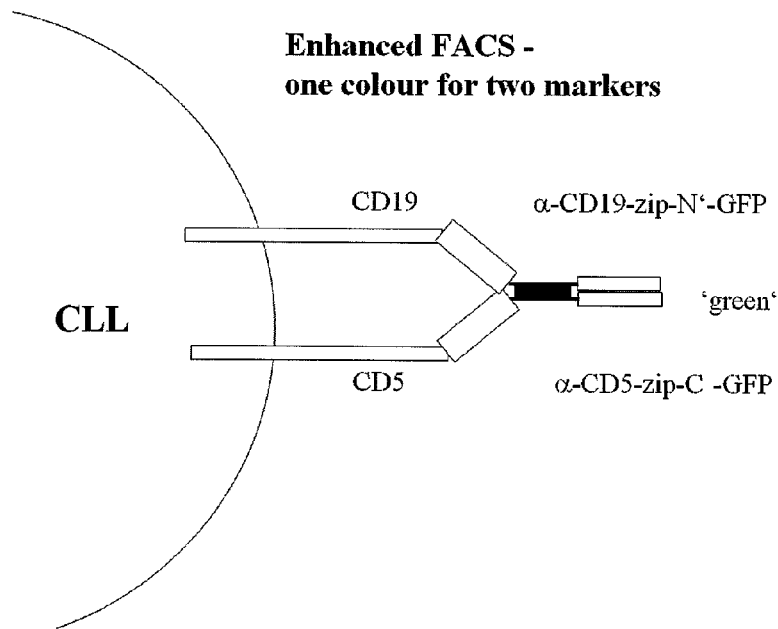
FIG. 16 (A) a diagrammatic representation of enhanced FACS with one color for two markers using demibodies. (B) Cell type-specific detection.

For FACS, the same combinations of antigens/epitopes are stained. Specially designed demibodies enable staining of combinations of antigens/epitopes with only one color and thus "free" other colors for additional antigens (e.g. CD4+ helper T cell: CD3 and CD4– actual red and green, with demibody only red or green). Demibodies forming different Fc-domains (e.g. IgG isotypes) allow differential labeling with secondary IgG subtype-specific antibodies. In combination with BiFC or even fluorescence resonance energy transfer (or Förster resonance energy transfer, FRET) instead of indirect labeling of the Fc domain with an labeled antibody, each scFv-fusion-protein could carry a part of a fluorescent protein, which after zipping would complement each other to a fluorescent protein (in case of FRET a complete fluorescence protein which in combination would allow FRET-transfer). See FIGS. 16A and B.

Fluorescence Microscopy

For fluorescence microscopy, the same reagents as for the FACS applications are used, including histology for clinical diagnostic purposes.

Immuno Assays

Figure 17:
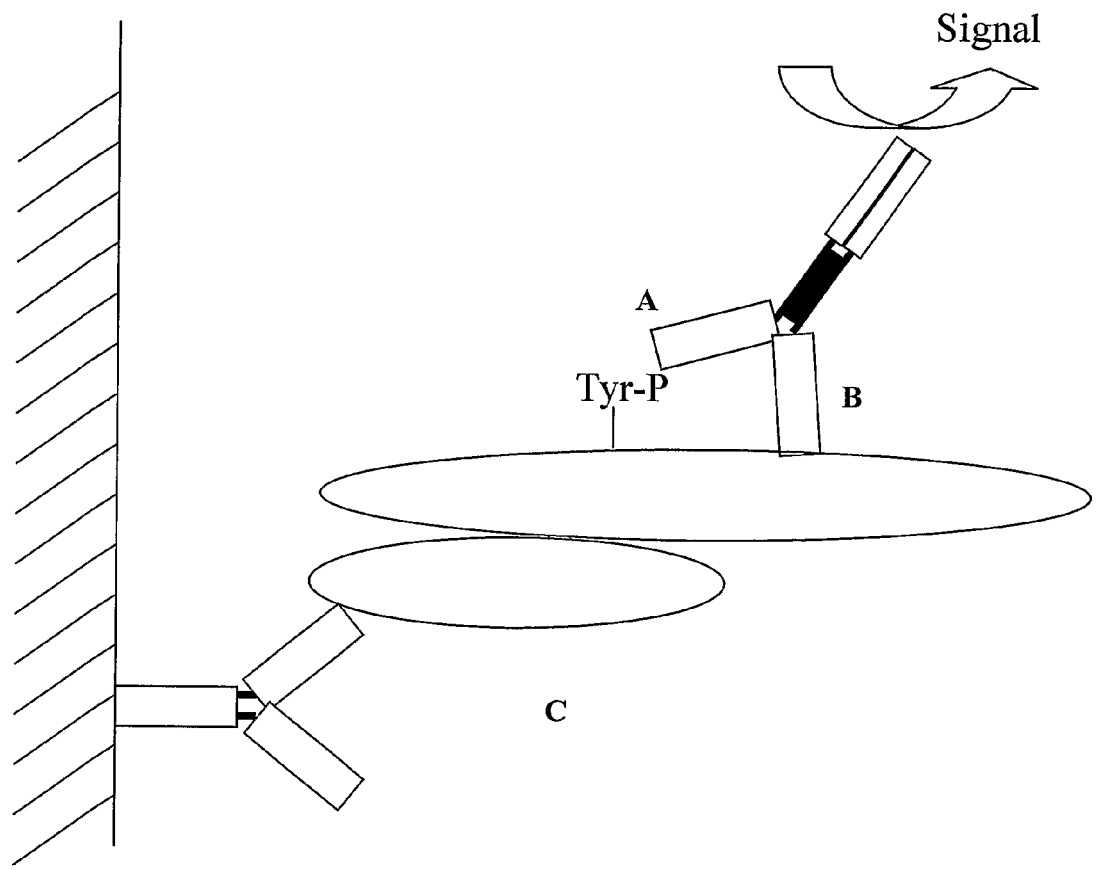
FIG. 17 is a diagrammatic representation showing enhanced immunoassays using demibodies where A=α-phospho-tyrosine, B=α-protein-epitope, and C=e.g. detection of multimeric modified proteins in one step.

Specially designed demibodies enable detection of multimeric modified proteins and allow their differentiation, e.g. phosphorylated proteins (1 scFv against phosphotyrosine, 1 scFv against the protein, capture antibody against second subunit), or glycosylated isoforms (1 scFv against sialic acid, 1 scFv against the protein, capture antibody against second subunit) [FIG. 17].

Research Tools

Demibody reagents useful for diagnostics also could be used in basic research as tools for e.g. advanced cell labeling and sorting, or novel antibody-based analyses.

Example: Protein Purification

Figure 18:
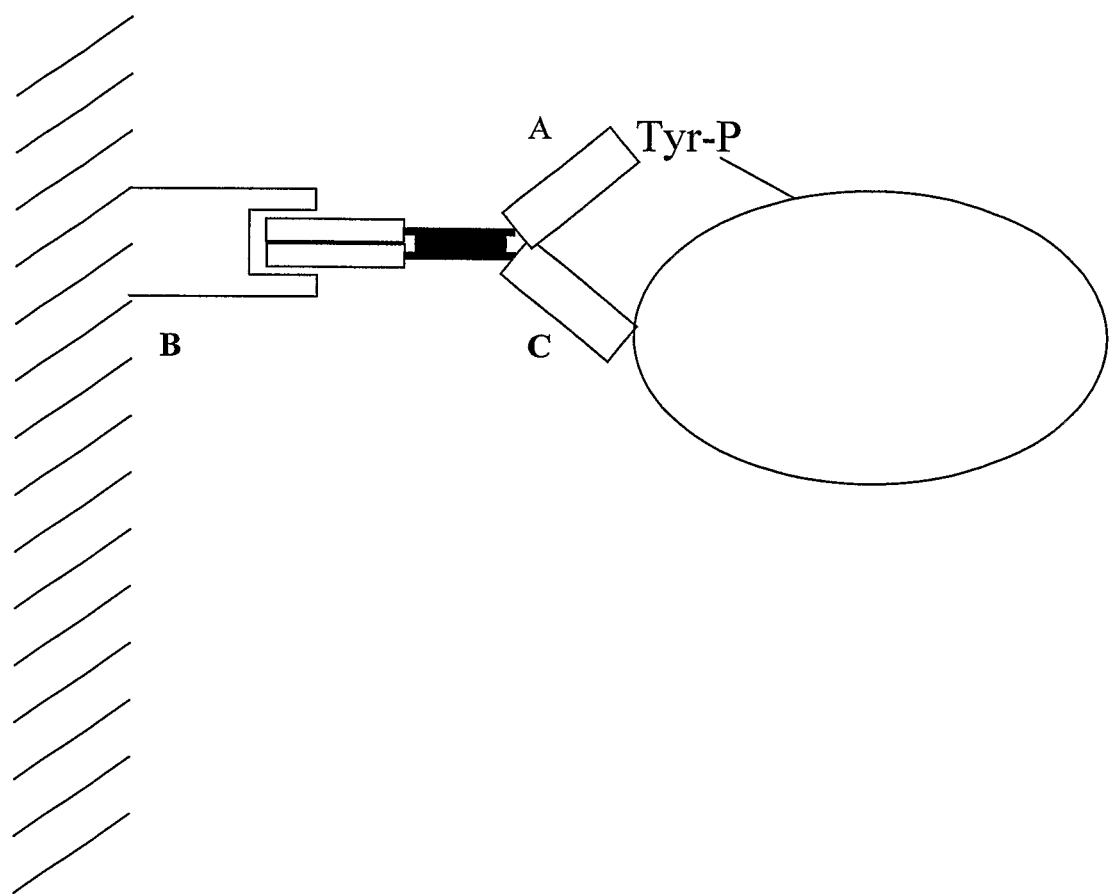
FIG. 18 is a diagrammatic representation showing enhanced immunoaffinity chromatography using demibodies where A=α-phospho-tyrosine, B=α-Fc, e.g. protein A, and C=α-protein-epitope.

Demibodies can be used for the purification of complexes, such a multimeric proteins, or modified proteins by affinity purification. An example would be the one-step purification of a phosphorylated protein (scFv anti-protein, scFv anti-phospho-tyrosine) [FIG. 18].

Example 7

Antibody-Dependent Cellular Cytotoxicity

Figure 19:
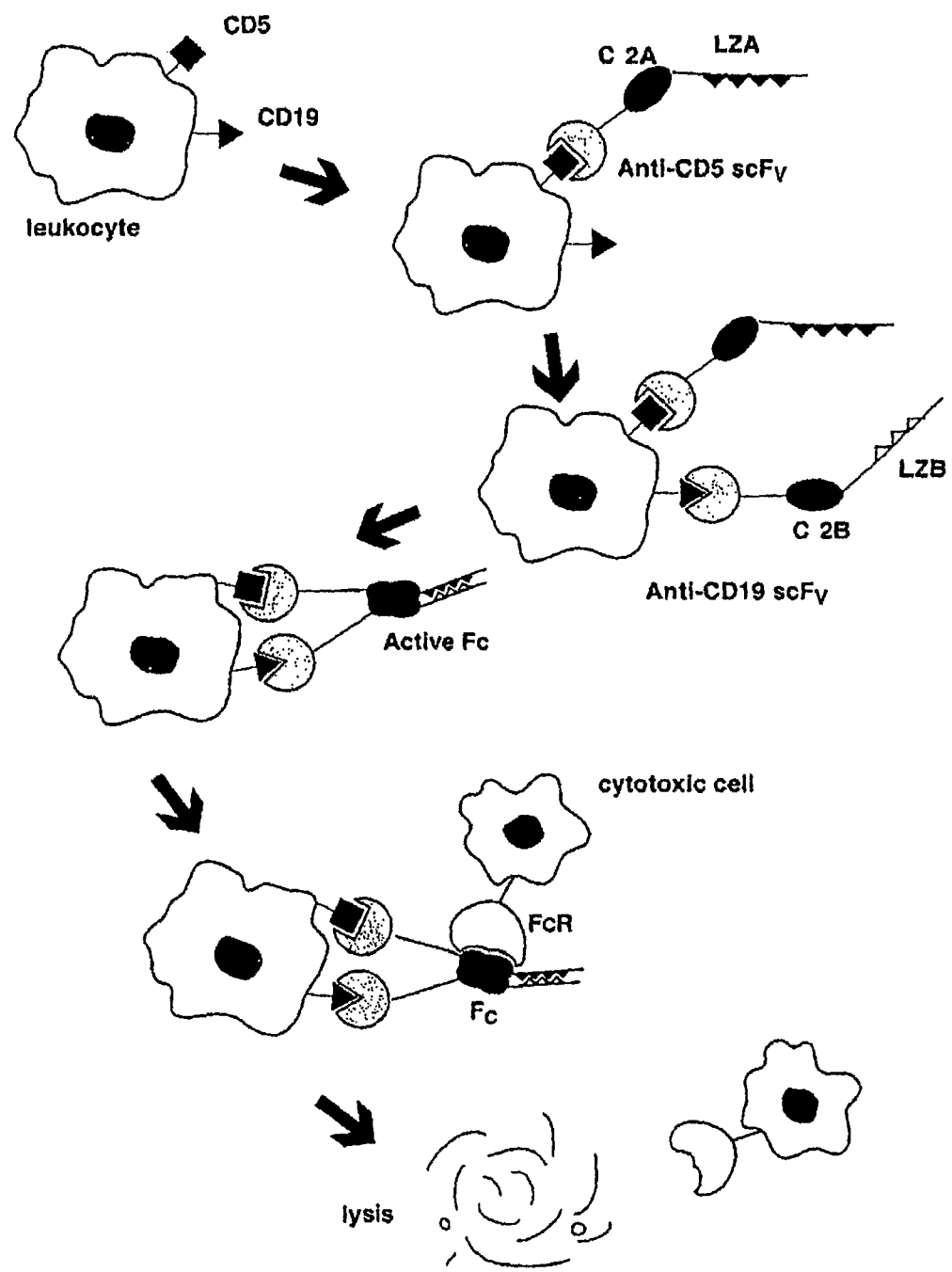
FIG. 19 is a diagrammatic representation showing antibody-dependent cellular cytotoxicity (ADCC) mediated against CD5$^+$ CD19$^+$ chronic lymphocytic leukemia (CLL) cells by a pair of demibodies.

FIG. 19 is a diagrammatic representation showing the use of two demibodies specific for CD5 or CD19. The demibodies comprise an scFv portion capable of binding to CD5 or CD19, an incomplete, non-functional Fc portion and half of a leucine zipper. The amino acid sequence of portions of the leucine zipper are shown in Table 3 (see SEQ ID NOs:1-5). Appropriate pairs include SEQ ID NOs:1 and 2, SEQ ID NOs:3 and 4 and SEQ ID NOs:3 and 5.

The two demibodies bind to a target cell expressing both CD5 and CD19. When the two bound demibodies come in close proximity, the leucine zipper portions interact and the two incomplete Fc portions form a functional Fc domain (see FIG. 19). A cytotoxic cell (e.g. neutrophil, macrophage, natural killer cell) with an Fc receptor (FcR; e.g. CD16, CD23, CD32, CD64, CD89) then mediates cell lysis.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Adams et al, *Nuc. Med. Biol.* 27:330-346, 2000
Bagshawe and Begent, *Adv. Drug Delivery Rev.* 22:365-367, 1996
Carter, *Nature Reviews* 1:118-128, 2001
Chames and Baty, *FEMS Microbiol. Lett.* 189:1-8, 2000
de Haard et al, *Adv. Drug Delivery Rev.* 31.5-31, 1998
de Kruif and Logtenberg, *J Biol Chem* 271:7630-7634, 1996
Funaro et al, *Biotechnol. Adv.* 18:385-401, 2000
Hudson, *Exp. Opin. Invest Drugs* 9: 1231-1242, 2000
Hudson and Souriau, *Nat Med* 9:129-134, 2003
Kreitman, *Curr. Opin. Immunol.* 11:570-578, 1999
Lin et al, *Cancer Res* 66:3884-92, 2006
Litowski and Hodges, *J. Biol. Chem.* 277:37272-37279, 2002
Reiter and Pastan, *Tibtech* 16:51-520, 1998
Shan et al, *J. Immunol* 162:6589-95, 1999
Shaner et al, *Nature Biotechnology* 22:1567-1572, 2004
Sondermann et al, *Nature* 406:267-273, 2000
Wu et al, *Immunotechnology* 2:21-36, 1996
Wu et al, *Proc. Natl. Acad. Sci. USA* 97:8495-8500, 2000
Zappater-Hommer and Griesbeck, *BMC Biotechnol* 3:5, 2003

The invention claimed is:

1. An isolated pair of demibodies comprising a first demibody and a second demibody, said first demibody comprising:
   an antigen-binding portion of a first immunoglobulin that interacts with a first antigen on a target cell;
   a first non-cytotoxic portion of an Fc domain; and
   a first member of a complementary leucine zipper pair;
said second demibody comprising:
   an antigen-binding portion of a second immunoglobulin that interacts with a second antigen on the target cell;
   a second non-cytotoxic portion of an Fc domain; and
   a second member of a complementary leucine zipper pair;
wherein the pair of demibodies is configured so that the first and second non-toxic portions of said first and second demibodies are only able to combine to generate a cytotoxic Fc domain after the first and second demibodies are bound to the first and second antigens on the target cell.

2. The pair of demibodies of claim 1 wherein the antigen-binding portions of the first and second immunoglobulins are single chain variable fragments (scFv).

3. The pair of demibodies of claim 1 wherein at least one of said antigen-binding portions of said first or second immunoglobulins is specific for a cluster of differentiation (CD) antigen.

4. The pair of demibodies of claim 1, wherein said cytotoxic Fc domain mediates complement-dependent cytotoxicity (CDC) or antibody-dependent cellular cytotoxicity (ADCC).

5. The pair of demibodies of claim 1, wherein said target cell is a cancer cell.

* * * * *